Figure 2A:
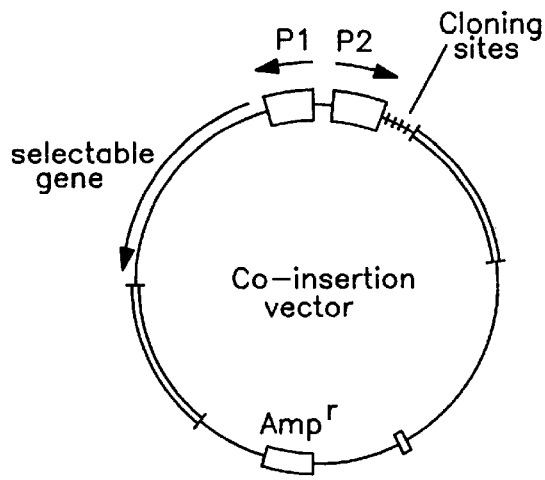

United States Patent [19]
Dale et al.

[11] Patent Number: 5,811,104
[45] Date of Patent: Sep. 22, 1998

[54] RECOMBINANT STRUCTURAL AND NON-STRUCTURAL PROTEINS OF FIPV AND METHOD OF IMMUNIZING

[75] Inventors: Beverly Dale, Los Altos; Miles Yamanaka, Walnut Creek, both of Calif.; William M. Acree; Lloyd G. Chavez, Jr., both of Fort Dodge, Iowa

[73] Assignees: American Home Products Corporation, Parsippany, N.J.; Scios, Inc., Mountain View, Calif.

[21] Appl. No.: 437,362

[22] Filed: May 9, 1995

Related U.S. Application Data

[62] Division of Ser. No. 220,401, Mar. 30, 1994, which is a continuation of Ser. No. 856,468, Mar. 24, 1992, abandoned, which is a continuation of Ser. No. 292,527, Dec. 30, 1988, abandoned.

[51] Int. Cl.$^6$ ................ A61K 39/215; A61K 39/12; C12N 15/00; C12N 15/09
[52] U.S. Cl. .................... 424/221.1; 424/199.1; 424/186.1; 424/204.1; 435/320.1; 435/69.3
[58] Field of Search ............... 424/186.1, 199.1, 424/221.1, 204.1; 435/69.3, 172.3, 235.1, 320.1, 252.3, 236; 536/23.72; 935/9, 12, 65; 530/403

[56] References Cited

FOREIGN PATENT DOCUMENTS

| 264 979 | 4/1988 | European Pat. Off. . |
|---|---|---|
| WO 87/04624 | 8/1987 | WIPO . |

OTHER PUBLICATIONS

August et al., "Feline Infectious Peritonitis", *Vet Clin North Am: Anim Pract* 14(5):975–984 (1984).
Barlough et al., "Feline Infectious Peritonitis", Churchhill Livingstone, New York, *Infectious Diseases* 3:93–108 (1986).
Barlough et al., "Experimental Inoculation of Cats with Canine Coronavirus and Subsequent Challenge with Feline Infectious Peritonitis Virus", *Lab Anim Sci* 34(6):592–597 (1984).
Woods et al., "Cross–Protection Studies Between Feline Infectious Peritonitis and Porcine Transmissible Gastroenteritis Viruses", *Vet Microbiol* 4:11–16 (1979).
Pedersen et al., "Attempted Immunization of Cats Against Feline Infectious Peritonitis, Using Avirulent Live Virus of Sublethal Amounts of Virulent Virus", *Am J Vet Res* 44(2):229–234 (1983).
Pederson et al., "Experimental Studies with Three New Strains of Feline Infectious Peritonitis Virus: FIPV–UCD2, FiPV–UCD3, and FIPV–UCD4",*Compendium on Continuing Education for the Practicing Veterinarian* 7:1001–1011 (1985).
De Groot et al., "cDNA Cloning and Sequence Analysis of the Gene Encoding the Peplomer Protein of Feline Infectious Peritonitis Virus", *J Gen Virol* 68:2639–2646 (1987).
R. J. DeGroot et al., "Sequence Analysis of the 3' End of the Feline Coronavirus FIPV 79–1146 Genome: Comparison with the Genome of Porcine Coronavirus TGEV Reveals Large Insertions", *Virology* 167:370–376 (1988).
R. J. DeGroot et al., "Intracellular RNAs of the Feline Infectious Peritonitis Coronavirus Strain 79–1146", *J Gen Virol* 68:995–1002 (1987).
S. A. Fiscus et al., "Competitive Enzyme Immunoassays for the Rapid Detection of Antibodies to Feline Infections Peritonits Virus Polypeptides",*Biological Abstracts,* vol. 80, Abstract No. 104471 (1985).
Luckow et al. "Trends in the Development of Baculovirus Expression Vectors". Biotechnology. Vol. 6:47–54, Jan. 1988.
Vennema et al. "Primary Structure of the Membrane and Nucleocapsid protein Genes of Feline Infectious Peritonitis and Immunogenicity of Recombinant Vaccinia Viruses Kittens". Virology. Vol. 181:327–335, 1991.
Wasmoen et al. "Protection of Cats From Infectious Peritonitis By Vaccination With a Recombinant Raccoon Poxvirus Expressing The Nucleocapsid Gene of Feline Infectious Peritonitis Virus". Corona and Related Viruses. Talbot et al, Eds. Plenum Press, Ny, pa, 1995.
Mackett et al. "Vaccinia Virus Expression Vectors". Journal of General Virology. Vol. 67, No. 10:2067–2082, 1986.
Kapke et al. "Nucleotide Sequence of the Porcine Transmissible Gastroenteritis Coronavirus Matrix Protein Gene". Adv. Exp. Med. Biol. vol. 218:117–122, 1987.
deGroot et al. "Intracellular RNAs of the Feline Infectious Coronavirus Strain 79–1146". Journal of General Virology. Vol. 68:995–1002, 1987a.
deGroot et al. "cDNA Cloning and sequence Analysis of the Gene Encoding the Peplomer Protein of Feline Infectious Peritonitis Virus". Journal of General Virology. Vol. 68:2639–2646, 1987b.
Lapps et al. "Sequence Analysis of the Bovine Coronavirus Nucleocapsid and Matrix protein Genes". Virology. Vol. 157: 47–57, 1987.
Rasschaert et al. "Enteric coronavirus TGEV: partial sequence of the genomic RNA, its organization and expression". Biochimie. Vol. 69:591–600, 1987.
Tomley et al. "Expression of the Infectious Bronchitis Virus Spike Protein by Recombinant Vaccinia Virus and Induction of Neutralizing Antibodies in Vaccinated Mice". Journal of General Virology. Vol. 68:2291–2298, 1987.
Ellis, Ronald. "New Technologies for Making Vaccines". Plotkin et al, Eds. Chapter 29, pp. 568–575, 1988.

*Primary Examiner*—Marian C. Knode
*Assistant Examiner*—Datquan Lee
*Attorney, Agent, or Firm*—Morrison & Foerster LLP

[57] ABSTRACT

The present invention relates to the development of an efficacious vaccine against Feline Infectious Peritonitis Virus (FIPV). The invention provides the tools for the synthesis and manipulation of the structural and non-structural proteins of FIPV. These proteins are able to elicit an immune response in cats against FIPV. The recombinant virus vectors which express the E1 or N proteins of the virus or the recombinant produced viral proteins themselves are able to elicit an immune response.

34 Claims, 5 Drawing Sheets

```
   1  TCTAGATGACAAGTTCTATTTGACCCCCAGAACTATGTATCAGCCTAGAGTTGCAACTAG    60
  61  TTCTGATTTTGTTCAAATTGAAGGGTGTGATGTGTTGTTTGTCAACGCGACTGTAATTGA   120
 121  TTTGCCTAGTATTATACCTGACTATATTGACATTAATCAAACTGTTCAAGACATATTAGA   180
 181  AAATTACAGACCAAACTGGACTGTACCTGAATTTACACTTGATATTTTCAACGCAACCTA   240
 241  TTTAAATCTGACTGGTGAAATTGATGACTTAGAGTTTAGGTCAGAAAAGCTACATAACAC   300
 301  TACAGTAGAACTTGCCATTCTCATTGATAACATTAATAATACATTAGTCAATCTTGAATG   360
 361  GCTCAATAGAATTGAAACTTATGTAAAATGGCCTTGGTATGTGTGGCTACTGATAGGTTT   420
 421  AGTAGTAGTATTTTGCATACCATTACTGCTATTTTGCTGTTTTAGCACAGGTTGTTGTGG   480
 481  ATGCATAGGTTGTTTAGGAAGTTGTTGTCACTCTATATGTAGTAGAAGACAATTTGAAAA   540
                                                              XmnI
 541  TTATGAACCAATTGAAAAAGTGCATGTCCACTAAATTTAAAGTTAAGGATGTTGAATAAA   600

NS2   TthIIII
 601  TTCCTTAAGAACTAAACTTATTAGTCATTACAGGTCTTGTATGGACATTGTCAAATCTAT   660
                                               MetAspIleValLysSerIl
 661  TGACATATTCGTAGACGCTGTACTTGACGAACTTGACCGTGCATACTTTGCTGTAACTCT   720
      eAspIlePheValAspAlaValLeuAspGluLeuAspArgAlaTyrPheAlaValThrLe

721  TAAAGTAGAATTTAAGACTGGTAAACTACTTGTGTGTATAGGTTTTGGTGACACACTTCT   780
      uLysValGluPheLysThrGlyLysLeuLeuValCysIleGlyPheGlyAspThrLeuLe

781  TGAGGCTAAGGACAAAGCGTATGCTAAGCTTGGTCTCTCCTTTATTGAAGAAGTCAATAG   840
      uGluAlaLysAspLysAlaTyrAlaLysLeuGlyLeuSerPheIleGluGluValAsnSe

841  TCATACAGTTGTTTAGTATTACTGTTTGAAACTAGACTTTGTATCATTAAACACACAAGA   900
      rHisThrValVal

901  CCCAAAGCATTAAGTGTTACAAAACAAGTAAAGAGAGATTATAGAAAAATTGCCATTCTA   960
 961  AATTCCATGCGAAAATGATTGGTGGACTTTTTCTTAACACTCTTAGTTTTGTAATTGTTA  1020
1021  TTAACCATGTTATTGTTAATAACACAGCAAATGTGCATACTACACAACATGAAAATGTTA  1080
1081  TAGTACAACAGCATTAGGTTGTTAGTGCTAGAACACAAAATTATTACCCAGAGTTCAGCA  1140
1141  TCGCTGTACTCTTTGTATCATTTTTGGCTTTGTACCGTAGTACAAACTTTAAGACGTGTG  1200
1201  TCGGCATCTTAATGTTTAAGATTGTATCAATGACACTTGTAGGGCCTATGCTTATAGCAT  1260
1261  ATGGTTACTACATTGATGGCATTGTTACAATAACTGTCTTAGCTTTAAGATTTTTCTACT  1320
1321  TAGCATACTTTTGGTATGTTAATAGTAGGTCGAATTTATTTTATACAATACAACGACAC   1380
1381  TCATGTTTGTACATGGCAGAGCTGCACCGTTTATGAGAAGTTCTCACAGCTCTATTTATG  1440
1441  TCACATTGTATGGTGGCATAAATTATATGTTTGTGAATGACCTCACGTTGCATTTTGTAG  1500
1501  ACCCTATGCTTGTAAGAATAGCAATACGTGGCTTAGCTCATGCTGATCTAACTGTTTTTA  1560
1561  GAGCAGTTGAACTTCTCAATGGTGATTTTATATATGTATTTTCACAGGAGCCGTAGCCGG  1620
1621  TGTTTACAATGCAGCCTCTTCTCAGGCGGTTCTAAACGAAATTGACTTAAAAGAAGAAGA  1680
1681  AGAAGACATAACTATGACGTTCCCTAGGGCATTTACTATCATAGATGACCATGGCATGG   1740
1741  TTGTTAGCGTCTTCTTCTGGCCTCCTGTTGATAATTATATTGATATTGTTTTCAATAGCAT  1800
1801  TGCTAAATGTTATTAAATTGTGCATGGTATGTTGCAATTTGGGTAAGACTATTATAGTAC  1860
1861  TACCTGCACGCCATGCATATGATGCCTATAAGACCTTTATGCAAATCAAGGCATATAATC  1920

[EcoRI]                          E1
1921  CCGACGAAGCATTTTTGGTTTGAACTAAACAAAATGAAGTACATTTTGCTAATACTCGCG  1980
                                       MetLysTyrIleLeuLeuIleLeuAla

1981  TGCATAATTGCATGCGTTTATGGTGAACGCTACTGTGCCATGCAAGACAGTGGCTTGCAG  2040
      CysIleIleAlaCysValTyrGlyGluArgTyrCysAlaMetGlnAspSerGlyLeuGln
```

FIG. IA

```
2041  TGTATTAATGGCACAAATTCAAGATGTCAAACCTGCTTTGAACGTGGTGATCTTATTTGG        2100
      CysIleAsnGlyThrAsnSerArgCysGlnThrCysPheGluArgGlyAspLeuIleTrp
                              PvuII
2101  CATCTTGCTAACTGGAACTTCAGCTGGTCTGTAATATTGATTGTTTTTATAACAGTGTTA        2160
      HisLeuAlaAsnTrpAsnPheSerTrpSerValIleLeuIleValPheIleThrValLeu
2161  CAATATGGCAGACCACAATTTAGCTGGCTCGTTTATGGCATTAAAATGCTGATCATGTGG        2220
      GlnTyrGlyArgProGlnPheSerTrpLeuValTyrGlyIleLysMetLeuIleMetTrp
2221  CTATTATGGCCTATTGTTCTAGCGCTTACGATTTTTAATGCATACTCTGAGTACCAAGTT        2280
      LeuLeuTrpProIleValLeuAlaLeuThrIlePheAsnAlaTyrSerGluTyrGlnVal
2281  TCCAGATATGTAATGTTCGGCTTTAGTGTTGCAGGTGCAGTTGTAACGTTTGCACTTTGG        2340
      SerArgTyrValMetPheGlyPheSerValAlaGlyAlaValValThrPheAlaLeuTrp
2341  ATGATGTATTTTGTGAGATCTGTTCAGCTATATAGAAGAACCAAATCATGGTGGTCTTTT        2400
      MetMetTyrPheValArgSerValGlnLeuTyrArgArgThrLysSerTrpTrpSerPhe
2401  AATCCTGAGACTAATGCAATTCTTTGTGTTAATGCATTGGGTAGAAGTTATGTGCTTCCC        2460
      AsnProGluThrAsnAlaIleLeuCysValAsnAlaLeuGlyArgSerTyrValLeuPro
2461  TTAGATGGTACTCCTACAGGTGTTACCCTTACTCTACTTTCAGGAAATCTATATGCTGAA        2520
      LeuAspGlyThrProThrGlyValThrLeuThrLeuLeuSerGlyAsnLeuTyrAlaGlu
2521  GGTTTCAAAATGGCTGGTGGTTTAACCATCGAGCATTTGCCTAAATACGTCATGATTGCT        2580
      GlyPheLysMetAlaGlyGlyLeuThrIleGluHisLeuProLysTyrValMetIleAla
2581  ACACCTAGTAGAACCATCGTTTATACATTAGTTGGAAAACAATTAAAAGCAACTACTGCC        2640
      ThrProSerArgThrIleValTyrThrLeuValGlyLysGlnLeuLysAlaThrThrAla
2641  ACAGGATGGGCTTACTACGTAAAATCTAAAGCTGGTGATTACTCAACAGAAGCACGTACT        2700
      ThrGlyTrpAlaTyrTyrValLysSerLysAlaGlyAspTyrSerThrGluAlaArgThr
                                                            N  BalI
2701  GACAATTTGAGTGAACATGAAAAATTATTACATATGGTGTAACTAAACTTTCAAATGGCC        2760
      AspAsnLeuSerGluHisGluLysLeuLeuHisMetVal             MetAla
          MluI
2761  ACACAGGGACAACGCGTCAACTGGGGAGATGAACCTTCCAAAAGACGTGGTCGTTCTAAC        2820
      ThrGlnGlyGlnArgValAsnTrpGlyAspGluProSerLysArgArgGlyArgSerAsn
2821  TCTCGTGGTCGGAAGAATAATGATATACCTTTGTCATTCTACAACCCCATTACCCTCGAA        2880
      SerArgGlyArgLysAsnAsnAspIleProLeuSerPheTyrAsnProIleThrLeuGlu
2881  CAAGGATCTAAATTTTGGAATTTATGTCCGAGAGACCTTGTTCCCAAAGGAATAGGTAAT        2940
      GlnGlySerLysPheTrpAsnLeuCysProArgAspLeuValProLysGlyIleGlyAsn
2941  AAGGATCAACAAATTGGTTATTGGAATAGACAGATTCGTTATCGTATTGTAAAAGGCCAG        3000
      LysAspGlnGlnIleGlyTyrTrpAsnArgGlnIleArgTyrArgIleValLysGlyGln
3001  CGTAAGGAACTCGCTGAGAGGTGGTTCTTTTACTTCTTAGGTACAGGACCTCATGCTGAT        3060
      ArgLysGluLeuAlaGluArgTrpPhePheTyrPheLeuGlyThrGlyProHisAlaAsp
3061  GCTAAATTCAAAGACAAGATTGATGGAGTCTTCTGGGTTGCAAGGGATGGTGCCATGAAC        3120
      AlaLysPheLysAspLysIleAspGlyValPheTrpValAlaArgAspGlyAlaMetAsn
```

FIG. IB

```
3121  AAGCCCACAACGCTTGGCACTCGTGGAACCAATAACGAATCCAAACCACTGAGATTTGAT  3180
      LysProThrThrLeuGlyThrArgGlyThrAsnAsnGluSerLysProLeuArgPheAsp

3181  GGTAAGATACCGCCACAGTTTCAGCTTGAAGTGAACCGTTCTAGGAACAATTCAAGGTCT  3240
      GlyLysIleProProGlnPheGlnLeuGluValAsnArgSerArgAsnAsnSerArgSer

3241  GGTTCTCAGTCTAGATCTGTTTCAAGAAACAGATCTCAATCTAGAGGAAGACACCATTCC  3300
      GlySerGlnSerArgSerValSerArgAsnArgSerGlnSerArgGlyArgHisHisSer

3301  AATAACCAGAATAATAATGTTGAGGATACAATTGTAGCCGTGCTTGAAAAATTAGGTGTT  3360
      AsnAsnGlnAsnAsnAsnValGluAspThrIleValAlaValLeuGluLysLeuGlyVal

3361  ACTGACAAACAAAGGTCACGTTCTAAACCTAGAGAACGTAGTGATTCCAAACCTAGGGAC  3420
      ThrAspLysGlnArgSerArgSerLysProArgGluArgSerAspSerLysProArgAsp

3421  ACAACACCTAAGAATGCCAACAAACACACCTGGAAGAAAACTGCAGGCAAGGGAGATGTG  3480
      ThrThrProLysAsnAlaAsnLysHisThrTrpLysLysThrAlaGlyLysGlyAspVal

3481  ACAACTTTCTATGGTGCTAGAAGTAGTTCAGCTAACTTTGGTGATAGTGATCTCGTTGCC  3540
      ThrThrPheTyrGlyAlaArgSerSerSerAlaAsnPheGlyAspSerAspLeuValAla

3541  AATGGTAACGCTGCCAAATGCTACCCTCAGATAGCTGAATGTGTTCCATCAGTGTCTAGC  3600
      AsnGlyAsnAlaAlaLysCysTyrProGlnIleAlaGluCysValProSerValSerSer

3601  ATAATCTTTGGCAGTCAATGGTCTGCTGAAGAAGCTGGTGATCAAGTGAAAGTCACGCTC  3660
      IleIlePheGlySerGlnTrpSerAlaGluGluAlaGlyAspGlnValLysValThrLeu

3661  ACTCACACCTACTACCTGCCAAAGGATGATGCCAAAACTAGTCAATTCCTAGAACAGATT  3720
      ThrHisThrTyrTyrLeuProLysAspAspAlaLysThrSerGlnPheLeuGluGlnIle

3721  GACGCTTACAAGCGACCTTCTGAAGTGGCTAAGGATCAGAGGCAAAGAAGATCCCGTTCT  3780
      AspAlaTyrLysArgProSerGluValAlaLysAspGlnArgGlnArgArgSerArgSer

3781  AAGTCTGCTGATAAGAAGCCTGAGGAGTTGTCTGTAACTCTTGTGGAGGCATACACAGAT  3840
      LysSerAlaAspLysLysProGluGluLeuSerValThrLeuValGluAlaTyrThrAsp

NSI  SphI
3841  GTGTTTGATGACACACAGGTTGAGATGATTGATGAGGTTACGAACTAAACGCATGCTCGT  3900
      ValPheAspAspThrGlnValGluMetIleAspGluValThrAsn         MetLeuVa

3901  TTTCGTCCATGCTGTACTTGTAACAGCTTTAATCTTACTACTAATTGGTAGAATCCAATT  3960
      lPheValHisAlaValLeuValThrAlaLeuIleLeuLeuLeuIleGlyArgIleGlnLe

3961  ACTAGAAAGGTTGTTACTCAGTCATCTGCTTAATCTTACAACAGTCAGTAATGTTTTAGG  4020
      uLeuGluArgLeuLeuLeuSerHisLeuLeuAsnLeuThrThrValSerAsnValLeuGl

4021  TGTGCCTGACAGTAGTCTGCGTGTAAATTGTTTGCAGCTTTTGAAACCAGACTGCCTTGA  4080
      yValProAspSerSerLeuArgValAsnCysLeuGlnLeuLeuLysProAspCysLeuAs

4081  TTTTAATATCTTACATAAAGTTTTAGCAGAAACCAGGTTACTAGTAGTAGTACTGCGAGT  4140
      pPheAsnIleLeuHisLysValLeuAlaGluThrArgLeuLeuValValValLeuArgVa

4141  GATCTTTCTAGTTCTTCTAGGGTTTTCCTGCTATACATTGTGGGTGCATTATTTTAACA  4200
      lIlePheLeuValLeuLeuGlyPheSerCysTyrThrLeuLeuGlyAlaLeuPhe
```

FIG. 1C

```
4201  TCATGATTGTTGTAATCCTTGTGTGTATCTTTTTGGCTAATGGAATTAAAGCTACTGCTG  4260
4261  TGCAAAATGACCTTCATGAACATCCCGTTCTTACCTGGGATTTATTACAGCATTTCATAG  4320
4321  GACATACCCTCTACATTACAACACACCAGGTCTTAGCACTACCGCTTGGATCTCGTGTTG  4380
4381  AGTGTGAGGGTATCGAAGGTTTCAATTGCACATGGCCTGGCTTTCAAGATCCTGCACATG  4440
4441  ATCATATTGATTTCTACTTTGATCTTTCTAATCCTTTCTATTCATTTGTAGATAATTTTT  4500
4501  ATATTGTAAGTGAGGGAAATCAAAGAATCAATCTCAGATTGGTTGGTGCTGTGCCAAAAC  4560
4561  AAAAGAGATTAAATGTTGGTTGTCATACATCATTTGCTGTTGATCTTCCATTTGGGATTC  4620
4621  AGATATACCATGACAGGGATTTTCAACACCCTGTTGATGGCAGACATCTAGATTGTACTC  4680
4681  ACAGAGTGTACTTTGTGAAGTACTGTCCACATAACCTGCATGGTTATTGCTTTAATGAGA  4740
4741  GGCTGAAAGTTTATGACTTGAAGCAATTCAGAAGCAAGAAGGTCTTCGACAAAATCAACC  4800
4801  AACATCATAAAACTGAGTTATAAGGCAACCCGATGTCTAAAACTGGTCTTTCCGAGGAAT  4860
4861  TACGGGTCATCGCGCTGCCTACTCTTGTACAGAATGGTAAGCACGTGTAATAGGAGGTAC  4920
4921  AAGCAACCCTATTGCATATTAGGAAGTTTAGATTTGATTTGGCAATGCTAGATTTAGTAA  4980
4981  TTTAGAGAAGTTTAAAGATCCGCTATGACGAGCCAACAATGGAAGAGCTAACGTCTGGAT  5040
5041  CTAGTGATTGTTTAAAATGTAAAATTGTTTGAAAATTTTCCTTTTGATAGTGATACACAA  5100
                                            EcoRI
5101  AAAAAAAAAAAAAAAAAAAAAAACCGAATTC   5130
```

FIG. ID

PLL promoter–ATG AAT TCC TGC AGG TCG ACT CTA GAG GAT CCC CGG G
                     Eco RI                                             Sma I

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 5130 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 641..853

( i x ) FEATURE:
        ( A ) NAME/KEY: CDS
        ( B ) LOCATION: 1954..2739

( i x ) FEATURE:
        ( A ) NAME/KEY: CDS
        ( B ) LOCATION: 2755..3885

( i x ) FEATURE:
        ( A ) NAME/KEY: CDS
        ( B ) LOCATION: 3893..4195

( x i ) SEQUENCE DESCRIPTION: SEQ ID NO:1:

```
TCTAGATGAC  AAGTTCTATT  TGACCCCCAG  AACTATGTAT  CAGCCTAGAG  TTGCAACTAG      60
TTCTGATTTT  GTTCAAATTG  AAGGGTGTGA  TGTGTTGTTT  GTCAACGCGA  CTGTAATTGA     120
TTTGCCTAGT  ATTATACCTG  ACTATATTGA  CATTAATCAA  ACTGTTCAAG  ACATATTAGA     180
AAATTACAGA  CCAAACTGGA  CTGTACCTGA  ATTTACACTT  GATATTTTCA  ACGCAACCTA     240
TTTAAATCTG  ACTGGTGAAA  TTGATGACTT  AGAGTTTAGG  TCAGAAAAGC  TACATAACAC     300
TACAGTAGAA  CTTGCCATTC  TCATTGATAA  CATTAATAAT  ACATTAGTCA  ATCTTGAATG     360
GCTCAATAGA  ATTGAAACTT  ATGTAAAATG  GCCTTGGTAT  GTGTGGCTAC  TGATAGGTTT     420
```

-continued

```
AGTAGTAGTA TTTTGCATAC CATTACTGCT ATTTTGCTGT TTTAGCACAG GTTGTTGTGG    480

ATGCATAGGT TGTTTAGGAA GTTGTTGTCA CTCTATATGT AGTAGAAGAC AATTTGAAAA    540

TTATGAACCA ATTGAAAAAG TGCATGTCCA CTAAATTTAA AGTTAAGGAT GTTGAATAAA    600

TTCCTTAAGA ACTAAACTTA TTAGTCATTA CAGGTCTTGT ATG GAC ATT GTC AAA      655
                                              Met Asp Ile Val Lys
                                                1               5

TCT ATT GAC ATA TTC GTA GAC GCT GTA CTT GAC GAA CTT GAC CGT GCA     703
Ser Ile Asp Ile Phe Val Asp Ala Val Leu Asp Glu Leu Asp Arg Ala
         10              15                     20

TAC TTT GCT GTA ACT CTT AAA GTA GAA TTT AAG ACT GGT AAA CTA CTT     751
Tyr Phe Ala Val Thr Leu Lys Val Glu Phe Lys Thr Gly Lys Leu Leu
             25              30                     35

GTG TGT ATA GGT TTT GGT GAC ACA CTT CTT GAG GCT AAG GAC AAA GCG     799
Val Cys Ile Gly Phe Gly Asp Thr Leu Leu Glu Ala Lys Asp Lys Ala
         40              45                     50

TAT GCT AAG CTT GGT CTC TCC TTT ATT GAA GAA GTC AAT AGT CAT ACA     847
Tyr Ala Lys Leu Gly Leu Ser Phe Ile Glu Glu Val Asn Ser His Thr
             55              60                     65

GTT GTT TAGTATTACT GTTTGAAACT AGACTTTGTA TCATTAAACA CACAAGACCC      903
Val Val
 70

AAAGCATTAA GTGTTACAAA ACAAGTAAAG AGAGATTATA GAAAAATTGC CATTCTAAAT    963

TCCATGCGAA AATGATTGGT GGACTTTTTC TTAACACTCT TAGTTTGTA ATTGTTATTA    1023

ACCATGTTAT TGTTAATAAC ACAGCAAATG TGCATACTAC ACAACATGAA ATGTTATAG    1083

TACAACAGCA TTAGGTTGTT AGTGCTAGAA CACAAAATTA TTACCCAGAG TTCAGCATCG   1143

CTGTACTCTT TGTATCATTT TTGGCTTTGT ACCGTAGTAC AAACTTTAAG ACGTGTGTCG   1203

GCATCTTAAT GTTTAAGATT GTATCAATGA CACTTGTAGG GCCTATGCTT ATAGCATATG   1263

GTTACTACAT TGATGGCATT GTTACAATAA CTGTCTTAGC TTTAAGATTT TTCTACTTAG   1323

CATACTTTTG GTATGTTAAT AGTAGGTCCG AATTTATTTT ATACAATACA ACGACACTCA   1383

TGTTTGTACA TGGCAGAGCT GCACCGTTTA TGAGAAGTTC TCACAGCTCT ATTTATGTCA   1443

CATTGTATGG TGGCATAAAT TATATGTTTG TGAATGACCT CACGTTGCAT TTTGTAGACC   1503

CTATGCTTGT AAGAATAGCA ATACGTGGCT TAGCTCATGC TGATCTAACT GTTTTAGAG    1563

CAGTTGAACT TCTCAATGGT GATTTTATAT ATGTATTTTC ACAGGAGCCG TAGCCGGTGT   1623

TTACAATGCA GCCTCTTCTC AGGCGGTTCT AAACGAAATT GACTTAAAAG AAGAAGAAGA   1683

AGACCATAAC TATGACGTTC CCTAGGGCAT TTACTATCAT AGATGACCAT GGCATGGTTG   1743

TTAGCGTCTT CTTCTGGCTC CTGTTGATAA TTATATTGAT ATTGTTTTCA ATAGCATTGC   1803

TAAATGTTAT TAAATTGTGC ATGGTATGTT GCAATTTGGG TAAGACTATT ATAGTACTAC   1863

CTGCACGCCA TGCATATGAT GCCTATAAGA CCTTTATGCA AATCAAGGCA TATAATCCCG   1923

ACGAAGCATT TTTGGTTTGA ACTAAACAAA ATG AAG TAC ATT TTG CTA ATA CTC    1977
                                 Met Lys Tyr Ile Leu Leu Ile Leu
                                   1               5

GCG TGC ATA ATT GCA TGC GTT TAT GGT GAA CGC TAC TGT GCC ATG CAA    2025
Ala Cys Ile Ile Ala Cys Val Tyr Gly Glu Arg Tyr Cys Ala Met Gln
         10              15                     20

GAC AGT GGC TTG CAG TGT ATT AAT GGC ACA AAT TCA AGA TGT CAA ACC    2073
Asp Ser Gly Leu Gln Cys Ile Asn Gly Thr Asn Ser Arg Cys Gln Thr
 25              30                      35                   40

TGC TTT GAA CGT GGT GAT CTT ATT TGG CAT CTT GCT AAC TGG AAC TTC    2121
Cys Phe Glu Arg Gly Asp Leu Ile Trp His Leu Ala Asn Trp Asn Phe
             45              50                     55
```

| | |
|---|---|
| AGC TGG TCT GTA ATA TTG ATT GTT TTT ATA ACA GTG TTA CAA TAT GGC<br>Ser Trp Ser Val Ile Leu Ile Val Phe Ile Thr Val Leu Gln Tyr Gly<br>              60                    65                    70 | 2169 |
| AGA CCA CAA TTT AGC TGG CTC GTT TAT GGC ATT AAA ATG CTG ATC ATG<br>Arg Pro Gln Phe Ser Trp Leu Val Tyr Gly Ile Lys Met Leu Ile Met<br>      75                    80                    85 | 2217 |
| TGG CTA TTA TGG CCT ATT GTT CTA GCG CTT ACG ATT TTT AAT GCA TAC<br>Trp Leu Leu Trp Pro Ile Val Leu Ala Leu Thr Ile Phe Asn Ala Tyr<br>        90                    95                  100 | 2265 |
| TCT GAG TAC CAA GTT TCC AGA TAT GTA ATG TTC GGC TTT AGT GTT GCA<br>Ser Glu Tyr Gln Val Ser Arg Tyr Val Met Phe Gly Phe Ser Val Ala<br>105                    110                 115               120 | 2313 |
| GGT GCA GTT GTA ACG TTT GCA CTT TGG ATG ATG TAT TTT GTG AGA TCT<br>Gly Ala Val Val Thr Phe Ala Leu Trp Met Met Tyr Phe Val Arg Ser<br>                  125                 130               135 | 2361 |
| GTT CAG CTA TAT AGA AGA ACC AAA TCA TGG TGG TCT TTT AAT CCT GAG<br>Val Gln Leu Tyr Arg Arg Thr Lys Ser Trp Trp Ser Phe Asn Pro Glu<br>                    140                 145               150 | 2409 |
| ACT AAT GCA ATT CTT TGT GTT AAT GCA TTG GGT AGA AGT TAT GTG CTT<br>Thr Asn Ala Ile Leu Cys Val Asn Ala Leu Gly Arg Ser Tyr Val Leu<br>155                    160                 165 | 2457 |
| CCC TTA GAT GGT ACT CCT ACA GGT GTT ACC CTT ACT CTA CTT TCA GGA<br>Pro Leu Asp Gly Thr Pro Thr Gly Val Thr Leu Thr Leu Leu Ser Gly<br>      170                    175                 180 | 2505 |
| AAT CTA TAT GCT GAA GGT TTC AAA ATG GCT GGT GGT TTA ACC ATC GAG<br>Asn Leu Tyr Ala Glu Gly Phe Lys Met Ala Gly Gly Leu Thr Ile Glu<br>185                    190               195               200 | 2553 |
| CAT TTG CCT AAA TAC GTC ATG ATT GCT ACA CCT AGT AGA ACC ATC GTT<br>His Leu Pro Lys Tyr Val Met Ile Ala Thr Pro Ser Arg Thr Ile Val<br>                    205                 210               215 | 2601 |
| TAT ACA TTA GTT GGA AAA CAA TTA AAA GCA ACT ACT GCC ACA GGA TGG<br>Tyr Thr Leu Val Gly Lys Gln Leu Lys Ala Thr Thr Ala Thr Gly Trp<br>                    220                 225               230 | 2649 |
| GCT TAC TAC GTA AAA TCT AAA GCT GGT GAT TAC TCA ACA GAA GCA CGT<br>Ala Tyr Tyr Val Lys Ser Lys Ala Gly Asp Tyr Ser Thr Glu Ala Arg<br>              235                    240               245 | 2697 |
| ACT GAC AAT TTG AGT GAA CAT GAA AAA TTA TTA CAT ATG GTG<br>Thr Asp Asn Leu Ser Glu His Glu Lys Leu Leu His Met Val<br>250                    255                 260 | 2739 |
| TAACTAAACT TTCAA ATG GCC ACA CAG GGA CAA CGC GTC AAC TGG GGA GAT<br>                            Met Ala Thr Gln Gly Gln Arg Val Asn Trp Gly Asp<br>                             1                    5                        10 | 2790 |
| GAA CCT TCC AAA AGA CGT GGT CGT TCT AAC TCT CGT GGT CGG AAG AAT<br>Glu Pro Ser Lys Arg Arg Gly Arg Ser Asn Ser Arg Gly Arg Lys Asn<br>              15                    20                    25 | 2838 |
| AAT GAT ATA CCT TTG TCA TTC TAC AAC CCC ATT ACC CTC GAA CAA GGA<br>Asn Asp Ile Pro Leu Ser Phe Tyr Asn Pro Ile Thr Leu Glu Gln Gly<br>      30                    35                    40 | 2886 |
| TCT AAA TTT TGG AAT TTA TGT CCG AGA GAC CTT GTT CCC AAA GGA ATA<br>Ser Lys Phe Trp Asn Leu Cys Pro Arg Asp Leu Val Pro Lys Gly Ile<br>45                    50                    55                  60 | 2934 |
| GGT AAT AAG GAT CAA CAA ATT GGT TAT TGG AAT AGA CAG ATT CGT TAT<br>Gly Asn Lys Asp Gln Gln Ile Gly Tyr Trp Asn Arg Gln Ile Arg Tyr<br>                    65                    70                    75 | 2982 |
| CGT ATT GTA AAA GGC CAG CGT AAG GAA CTC GCT GAG AGG TGG TTC TTT<br>Arg Ile Val Lys Gly Gln Arg Lys Glu Leu Ala Glu Arg Trp Phe Phe<br>            80                      85                    90 | 3030 |
| TAC TTC TTA GGT ACA GGA CCT CAT GCT GAT GCT AAA TTC AAA GAC AAG<br>Tyr Phe Leu Gly Thr Gly Pro His Ala Asp Ala Lys Phe Lys Asp Lys<br>                95                    100                 105 | 3078 |

| | | | | | | | | | | | | | | | | |
|---|---|---|---|---|---|---|---|---|---|---|---|---|---|---|---|---|
| ATT | GAT | GGA | GTC | TTC | TGG | GTT | GCA | AGG | GAT | GGT | GCC | ATG | AAC | AAG | CCC | 3126 |
| Ile | Asp | Gly | Val | Phe | Trp | Val | Ala | Arg | Asp | Gly | Ala | Met | Asn | Lys | Pro | |
| | | 110 | | | | 115 | | | | | 120 | | | | | |
| ACA | ACG | CTT | GGC | ACT | CGT | GGA | ACC | AAT | AAC | GAA | TCC | AAA | CCA | CTG | AGA | 3174 |
| Thr | Thr | Leu | Gly | Thr | Arg | Gly | Thr | Asn | Asn | Glu | Ser | Lys | Pro | Leu | Arg | |
| 125 | | | | | 130 | | | | | 135 | | | | | 140 | |
| TTT | GAT | GGT | AAG | ATA | CCG | CCA | CAG | TTT | CAG | CTT | GAA | GTG | AAC | CGT | TCT | 3222 |
| Phe | Asp | Gly | Lys | Ile | Pro | Pro | Gln | Phe | Gln | Leu | Glu | Val | Asn | Arg | Ser | |
| | | | | 145 | | | | | 150 | | | | | 155 | | |
| AGG | AAC | AAT | TCA | AGG | TCT | GGT | TCT | CAG | TCT | AGA | TCT | GTT | TCA | AGA | AAC | 3270 |
| Arg | Asn | Asn | Ser | Arg | Ser | Gly | Ser | Gln | Ser | Arg | Ser | Val | Ser | Arg | Asn | |
| | | | 160 | | | | | 165 | | | | | 170 | | | |
| AGA | TCT | CAA | TCT | AGA | GGA | AGA | CAC | CAT | TCC | AAT | AAC | CAG | AAT | AAT | AAT | 3318 |
| Arg | Ser | Gln | Ser | Arg | Gly | Arg | His | His | Ser | Asn | Asn | Gln | Asn | Asn | Asn | |
| | | 175 | | | | | 180 | | | | | 185 | | | | |
| GTT | GAG | GAT | ACA | ATT | GTA | GCC | GTG | CTT | GAA | AAA | TTA | GGT | GTT | ACT | GAC | 3366 |
| Val | Glu | Asp | Thr | Ile | Val | Ala | Val | Leu | Glu | Lys | Leu | Gly | Val | Thr | Asp | |
| | 190 | | | | | 195 | | | | | 200 | | | | | |
| AAA | CAA | AGG | TCA | CGT | TCT | AAA | CCT | AGA | GAA | CGT | AGT | GAT | TCC | AAA | CCT | 3414 |
| Lys | Gln | Arg | Ser | Arg | Ser | Lys | Pro | Arg | Glu | Arg | Ser | Asp | Ser | Lys | Pro | |
| 205 | | | | | 210 | | | | | 215 | | | | | 220 | |
| AGG | GAC | ACA | ACA | CCT | AAG | AAT | GCC | AAC | AAA | CAC | ACC | TGG | AAG | AAA | ACT | 3462 |
| Arg | Asp | Thr | Thr | Pro | Lys | Asn | Ala | Asn | Lys | His | Thr | Trp | Lys | Lys | Thr | |
| | | | | 225 | | | | | 230 | | | | | 235 | | |
| GCA | GGC | AAG | GGA | GAT | GTG | ACA | ACT | TTC | TAT | GGT | GCT | AGA | AGT | AGT | TCA | 3510 |
| Ala | Gly | Lys | Gly | Asp | Val | Thr | Thr | Phe | Tyr | Gly | Ala | Arg | Ser | Ser | Ser | |
| | | | 240 | | | | | 245 | | | | | 250 | | | |
| GCT | AAC | TTT | GGT | GAT | AGT | GAT | CTC | GTT | GCC | AAT | GGT | AAC | GCT | GCC | AAA | 3558 |
| Ala | Asn | Phe | Gly | Asp | Ser | Asp | Leu | Val | Ala | Asn | Gly | Asn | Ala | Ala | Lys | |
| | | 255 | | | | | 260 | | | | | 265 | | | | |
| TGC | TAC | CCT | CAG | ATA | GCT | GAA | TGT | GTT | CCA | TCA | GTG | TCT | AGC | ATA | ATC | 3606 |
| Cys | Tyr | Pro | Gln | Ile | Ala | Glu | Cys | Val | Pro | Ser | Val | Ser | Ser | Ile | Ile | |
| | 270 | | | | | 275 | | | | | 280 | | | | | |
| TTT | GGC | AGT | CAA | TGG | TCT | GCT | GAA | GAA | GCT | GGT | GAT | CAA | GTG | AAA | GTC | 3654 |
| Phe | Gly | Ser | Gln | Trp | Ser | Ala | Glu | Glu | Ala | Gly | Asp | Gln | Val | Lys | Val | |
| 285 | | | | | 290 | | | | | 295 | | | | | 300 | |
| ACG | CTC | ACT | CAC | ACC | TAC | TAC | CTG | CCA | AAG | GAT | GAT | GCC | AAA | ACT | AGT | 3702 |
| Thr | Leu | Thr | His | Thr | Tyr | Tyr | Leu | Pro | Lys | Asp | Asp | Ala | Lys | Thr | Ser | |
| | | | | 305 | | | | | 310 | | | | | 315 | | |
| CAA | TTC | CTA | GAA | CAG | ATT | GAC | GCT | TAC | AAG | CGA | CCT | TCT | GAA | GTG | GCT | 3750 |
| Gln | Phe | Leu | Glu | Gln | Ile | Asp | Ala | Tyr | Lys | Arg | Pro | Ser | Glu | Val | Ala | |
| | | | | 320 | | | | | 325 | | | | | 330 | | |
| AAG | GAT | CAG | AGG | CAA | AGA | AGA | TCC | CGT | TCT | AAG | TCT | GCT | GAT | AAG | AAG | 3798 |
| Lys | Asp | Gln | Arg | Gln | Arg | Arg | Ser | Arg | Ser | Lys | Ser | Ala | Asp | Lys | Lys | |
| | | 335 | | | | | 340 | | | | | 345 | | | | |
| CCT | GAG | GAG | TTG | TCT | GTA | ACT | CTT | GTG | GAG | GCA | TAC | ACA | GAT | GTG | TTT | 3846 |
| Pro | Glu | Glu | Leu | Ser | Val | Thr | Leu | Val | Glu | Ala | Tyr | Thr | Asp | Val | Phe | |
| | 350 | | | | | 355 | | | | | 360 | | | | | |
| GAT | GAC | ACA | CAG | GTT | GAG | ATG | ATT | GAT | GAG | GTT | ACG | AAC | TAAACGC | | ATG | 3895 |
| Asp | Asp | Thr | Gln | Val | Glu | Met | Ile | Asp | Glu | Val | Thr | Asn | | | Met | |
| 365 | | | | | 370 | | | | | 375 | | | | | 1 | |
| CTC | GTT | TTC | GTC | CAT | GCT | GTA | CTT | GTA | ACA | GCT | TTA | ATC | TTA | CTA | CTA | 3943 |
| Leu | Val | Phe | Val | His | Ala | Val | Leu | Val | Thr | Ala | Leu | Ile | Leu | Leu | Leu | |
| | | | | 5 | | | | | 10 | | | | | 15 | | |
| ATT | GGT | AGA | ATC | CAA | TTA | CTA | GAA | AGG | TTG | TTA | CTC | AGT | CAT | CTG | CTT | 3991 |
| Ile | Gly | Arg | Ile | Gln | Leu | Leu | Glu | Arg | Leu | Leu | Leu | Ser | His | Leu | Leu | |
| | | 20 | | | | | 25 | | | | | 30 | | | | |
| AAT | CTT | ACA | ACA | GTC | AGT | AAT | GTT | TTA | GGT | GTG | CCT | GAC | AGT | AGT | CTG | 4039 |
| Asn | Leu | Thr | Thr | Val | Ser | Asn | Val | Leu | Gly | Val | Pro | Asp | Ser | Ser | Leu | |
| | | 35 | | | | | 40 | | | | | 45 | | | | |

```
CGT  GTA  AAT  TGT  TTG  CAG  CTT  TTG  AAA  CCA  GAC  TGC  CTT  GAT  TTT  AAT           4087
Arg  Val  Asn  Cys  Leu  Gln  Leu  Leu  Lys  Pro  Asp  Cys  Leu  Asp  Phe  Asn
50                      55                      60                      65

ATC  TTA  CAT  AAA  GTT  TTA  GCA  GAA  ACC  AGG  TTA  CTA  GTA  GTA  GTA  CTG           4135
Ile  Leu  His  Lys  Val  Leu  Ala  Glu  Thr  Arg  Leu  Leu  Val  Val  Val  Leu
                    70                      75                          80

CGA  GTG  ATC  TTT  CTA  GTT  CTT  CTA  GGG  TTT  TCC  TGC  TAT  ACA  TTG  TTG           4183
Arg  Val  Ile  Phe  Leu  Val  Leu  Leu  Gly  Phe  Ser  Cys  Tyr  Thr  Leu  Leu
               85                       90                      95

GGT  GCA  TTA  TTT   TAACATCATG  ATTGTTGTAA  TCCTTGTGTG  TATCTTTTG                         4235
Gly  Ala  Leu  Phe
               100
```

GCTAATGGAA TTAAAGCTAC TGCTGTGCAA AATGACCTTC ATGAACATCC CGTTCTTACC 4295
TGGGATTTAT TACAGCATTT CATAGGACAT ACCCTCTACA TTACAACACA CCAGGTCTTA 4355
GCACTACCGC TTGGATCTCG TGTTGAGTGT GAGGGTATCG AAGGTTTCAA TTGCACATGG 4415
CCTGGCTTTC AAGATCCTGC ACATGATCAT ATTGATTTCT ACTTTGATCT TTCTAATCCT 4475
TTCTATTCAT TTGTAGATAA TTTTTATATT GTAAGTGAGG GAAATCAAAG AATCAATCTC 4535
AGATTGGTTG GTGCTGTGCC AAAACAAAAG AGATTAAATG TTGGTTGTCA TACATCATTT 4595
GCTGTTGATC TTCCATTTGG GATTCAGATA TACCATGACA GGGATTTTCA ACACCCTGTT 4655
GATGGCAGAC ATCTAGATTG TACTCACAGA GTGTACTTTG TGAAGTACTG TCCACATAAC 4715
CTGCATGGTT ATTGCTTTAA TGAGAGGCTG AAAGTTTATG ACTTGAAGCA ATTCAGAAGC 4775
AAGAAGGTCT TCGACAAAAT CAACCAACAT CATAAAACTG AGTTATAAGG CAACCCGATG 4835
TCTAAAACTG GTCTTTCCGA GGAATTACGG GTCATCGCGC TGCCTACTCT TGTACAGAAT 4895
GGTAAGCACG TGTAATAGGA GGTACAAGCA ACCCTATTGC ATATTAGGAA GTTTAGATTT 4955
GATTTGGCAA TGCTAGATTT AGTAATTTAG AGAAGTTTAA AGATCCGCTA TGACGAGCCA 5015
ACAATGGAAG AGCTAACGTC TGGATCTAGT GATTGTTTAA AATGTAAAAT TGTTTGAAAA 5075
TTTTCCTTTT GATAGTGATA CACAAAAAAA AAAAAAAAA AAAAAACCG AATTC 5130

( 2 ) INFORMATION FOR SEQ ID NO:2:

( i ) SEQUENCE CHARACTERISTICS:
        ( A ) LENGTH: 71 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Ile  Val  Lys  Ser  Ile  Asp  Ile  Phe  Val  Asp  Ala  Val  Leu  Asp
1                   5                    10                      15

Glu  Leu  Asp  Arg  Ala  Tyr  Phe  Ala  Val  Thr  Leu  Lys  Val  Glu  Phe  Lys
               20                       25                      30

Thr  Gly  Lys  Leu  Leu  Val  Cys  Ile  Gly  Phe  Gly  Asp  Thr  Leu  Leu  Glu
          35                       40                      45

Ala  Lys  Asp  Lys  Ala  Tyr  Ala  Lys  Leu  Gly  Leu  Ser  Phe  Ile  Glu  Glu
     50                       55                      60

Val  Asn  Ser  His  Thr  Val  Val
65                      70
```

( 2 ) INFORMATION FOR SEQ ID NO:3:

( i ) SEQUENCE CHARACTERISTICS:
        ( A ) LENGTH: 262 amino acids
        ( B ) TYPE: amino acid (D) TOPOLOGY: linear (ii) MOLECULE TYPE: protein (xi) SEQUENCE DESCRIPTION: SEQ ID NO:3:

| Met 1 | Lys | Tyr | Ile | Leu 5 | Leu | Ile | Leu | Ala | Cys 10 | Ile | Ile | Ala | Cys | Val 15 | Tyr |
|---|---|---|---|---|---|---|---|---|---|---|---|---|---|---|---|
| Gly | Glu | Arg | Tyr 20 | Cys | Ala | Met | Gln | Asp 25 | Ser | Gly | Leu | Gln | Cys 30 | Ile | Asn |
| Gly | Thr | Asn 35 | Ser | Arg | Cys | Gln | Thr 40 | Cys | Phe | Glu | Arg | Gly 45 | Asp | Leu | Ile |
| Trp | His 50 | Leu | Ala | Asn | Trp | Asn 55 | Phe | Ser | Trp | Ser | Val 60 | Ile | Leu | Ile | Val |
| Phe 65 | Ile | Thr | Val | Leu | Gln 70 | Tyr | Gly | Arg | Pro | Gln 75 | Phe | Ser | Trp | Leu | Val 80 |
| Tyr | Gly | Ile | Lys | Met 85 | Leu | Ile | Met | Trp | Leu 90 | Leu | Trp | Pro | Ile | Val 95 | Leu |
| Ala | Leu | Thr | Ile 100 | Phe | Asn | Ala | Tyr | Ser 105 | Glu | Tyr | Gln | Val | Ser 110 | Arg | Tyr |
| Val | Met | Phe 115 | Gly | Phe | Ser | Val | Ala 120 | Gly | Ala | Val | Val | Thr 125 | Phe | Ala | Leu |
| Trp | Met 130 | Met | Tyr | Phe | Val | Arg 135 | Ser | Val | Gln | Leu | Tyr 140 | Arg | Arg | Thr | Lys |
| Ser 145 | Trp | Trp | Ser | Phe | Asn 150 | Pro | Glu | Thr | Asn | Ala 155 | Ile | Leu | Cys | Val | Asn 160 |
| Ala | Leu | Gly | Arg | Ser 165 | Tyr | Val | Leu | Pro | Leu 170 | Asp | Gly | Thr | Pro | Thr 175 | Gly |
| Val | Thr | Leu | Thr 180 | Leu | Leu | Ser | Gly | Asn 185 | Leu | Tyr | Ala | Glu | Gly 190 | Phe | Lys |
| Met | Ala | Gly 195 | Gly | Leu | Thr | Ile | Glu 200 | His | Leu | Pro | Lys | Tyr 205 | Val | Met | Ile |
| Ala | Thr 210 | Pro | Ser | Arg | Thr | Ile 215 | Val | Tyr | Thr | Leu | Val 220 | Gly | Lys | Gln | Leu |
| Lys 225 | Ala | Thr | Thr | Ala | Thr 230 | Gly | Trp | Ala | Tyr | Tyr 235 | Val | Lys | Ser | Lys | Ala 240 |
| Gly | Asp | Tyr | Ser | Thr 245 | Glu | Ala | Arg | Thr | Asp 250 | Asn | Leu | Ser | Glu 255 | His | Glu |
| Lys | Leu | Leu | His 260 | Met | Val | | | | | | | | | | |

(2) INFORMATION FOR SEQ ID NO:4:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO:4:

| Met 1 | Ala | Thr | Gln | Gly 5 | Gln | Arg | Val | Asn | Trp 10 | Gly | Asp | Glu | Pro | Ser 15 | Lys |
|---|---|---|---|---|---|---|---|---|---|---|---|---|---|---|---|
| Arg | Arg | Gly | Arg 20 | Ser | Asn | Ser | Arg | Gly 25 | Arg | Lys | Asn | Asn | Asp 30 | Ile | Pro |
| Leu | Ser | Phe 35 | Tyr | Asn | Pro | Ile | Thr 40 | Leu | Glu | Gln | Gly | Ser 45 | Lys | Phe | Trp |
| Asn | Leu 50 | Cys | Pro | Arg | Asp | Leu 55 | Val | Pro | Lys | Gly | Ile 60 | Gly | Asn | Lys | Asp |

```
Gln  Gln  Ile  Gly  Tyr  Trp  Asn  Arg  Gln  Ile  Arg  Tyr  Arg  Ile  Val  Lys
 65             70                  75                      80

Gly  Gln  Arg  Lys  Glu  Leu  Ala  Glu  Arg  Trp  Phe  Phe  Tyr  Phe  Leu  Gly
              85                  90                      95

Thr  Gly  Pro  His  Ala  Asp  Ala  Lys  Phe  Lys  Asp  Lys  Ile  Asp  Gly  Val
              100                     105                    110

Phe  Trp  Val  Ala  Arg  Asp  Gly  Ala  Met  Asn  Lys  Pro  Thr  Thr  Leu  Gly
              115                     120                    125

Thr  Arg  Gly  Thr  Asn  Asn  Glu  Ser  Lys  Pro  Leu  Arg  Phe  Asp  Gly  Lys
     130                     135                    140

Ile  Pro  Pro  Gln  Phe  Gln  Leu  Glu  Val  Asn  Arg  Ser  Arg  Asn  Asn  Ser
145                      150                    155                      160

Arg  Ser  Gly  Ser  Gln  Ser  Arg  Ser  Val  Ser  Arg  Asn  Arg  Ser  Gln  Ser
               165                      170                    175

Arg  Gly  Arg  His  His  Ser  Asn  Asn  Gln  Asn  Asn  Asn  Val  Glu  Asp  Thr
               180                      185                    190

Ile  Val  Ala  Val  Leu  Glu  Lys  Leu  Gly  Val  Thr  Asp  Lys  Gln  Arg  Ser
               195                      200                    205

Arg  Ser  Lys  Pro  Arg  Glu  Arg  Ser  Asp  Ser  Lys  Pro  Arg  Asp  Thr  Thr
     210                      215                    220

Pro  Lys  Asn  Ala  Asn  Lys  His  Thr  Trp  Lys  Lys  Thr  Ala  Gly  Lys  Gly
225                      230                      235                         240

Asp  Val  Thr  Thr  Phe  Tyr  Gly  Ala  Arg  Ser  Ser  Ala  Asn  Phe  Gly
               245                      250                    255

Asp  Ser  Asp  Leu  Val  Ala  Asn  Gly  Asn  Ala  Ala  Lys  Cys  Tyr  Pro  Gln
               260                      265                    270

Ile  Ala  Glu  Cys  Val  Pro  Ser  Val  Ser  Ser  Ile  Ile  Phe  Gly  Ser  Gln
               275                      280                    285

Trp  Ser  Ala  Glu  Glu  Ala  Gly  Asp  Gln  Val  Lys  Val  Thr  Leu  Thr  His
     290                      295                    300

Thr  Tyr  Tyr  Leu  Pro  Lys  Asp  Asp  Ala  Lys  Thr  Ser  Gln  Phe  Leu  Glu
305                      310                      315                         320

Gln  Ile  Asp  Ala  Tyr  Lys  Arg  Pro  Ser  Glu  Val  Ala  Lys  Asp  Gln  Arg
               325                      330                    335

Gln  Arg  Arg  Ser  Arg  Ser  Lys  Ser  Ala  Asp  Lys  Lys  Pro  Glu  Glu  Leu
               340                      345                    350

Ser  Val  Thr  Leu  Val  Glu  Ala  Tyr  Thr  Asp  Val  Phe  Asp  Asp  Thr  Gln
               355                      360                    365

Val  Glu  Met  Ile  Asp  Glu  Val  Thr  Asn
     370                      375
```

( 2 ) INFORMATION FOR SEQ ID NO:5:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Leu  Val  Phe  Val  His  Ala  Val  Leu  Val  Thr  Ala  Leu  Ile  Leu  Leu
  1             5                      10                         15

Leu  Ile  Gly  Arg  Ile  Gln  Leu  Leu  Glu  Arg  Leu  Leu  Leu  Ser  His  Leu
               20                      25                         30
```

```
Leu Asn Leu Thr Thr Val Ser Asn Val Leu Gly Val Pro Asp Ser Ser
             35                  40                  45
Leu Arg Val Asn Cys Leu Gln Leu Leu Lys Pro Asp Cys Leu Asp Phe
         50                  55                  60
Asn Ile Leu His Lys Val Leu Ala Glu Thr Arg Leu Leu Val Val Val
 65                      70                  75                  80
Leu Arg Val Ile Phe Leu Val Leu Leu Gly Phe Ser Cys Tyr Thr Leu
                 85                  90                  95
Leu Gly Ala Leu Phe
            100
```

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ATGAATTCCT GCAGGTCGAC TCTAGAGGAT CCCCGGG      37

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCGTAAGCGC TAGAACAA      18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AACTGTGTGG TATGAACA      18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TACGTTAACT TGTATGCA      18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AGAGCAGTTG TACCACAC      18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

ATTATCAGAC GGTACACC              18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

GTAATCTGTA CAGGAGTC              18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

CAGCCTATCA ACTTGTGC              18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:14:

TTGTCTGGTT AGAGTCTG              18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

TCTAGGCTGA TACATAGT              18

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:16:

Met  Asn  Phe  Val  Lys
    1                        5

(2) INFORMATION FOR SEQ ID NO:17:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:17:

Met Asn Ser Thr Gln
1               5

(2) INFORMATION FOR SEQ ID NO:18:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:18:

Met Asn Ser Met Leu Val Phe
1               5

(2) INFORMATION FOR SEQ ID NO:19:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:19:

Met Ile Val Leu Val
1               5

(2) INFORMATION FOR SEQ ID NO:20:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:20:

Met Asn Ser Leu Val
1               5

RECOMBINANT STRUCTURAL AND NON-STRUCTURAL PROTEINS OF FIPV AND METHOD OF IMMUNIZING

This application is a divisional of application Ser. No. 08/220,401, filed 30 Mar. 1994, pending, which is a continuation of Ser. No. 07/856,468 filed 24 Mar. 1992, abandoned, which is a continuation of Ser. No. 07/292,527 filed 30 Dec. 1988, abandoned.

TECHNICAL FIELD OF THE INVENTION

The invention is in the fields of recombinant DNA technology and immunoprevention of viral diseases. More particularly, it relates to feline infectious peritonitis (FIP), recombinantly produced-proteins of FIP virus, and uses thereof in diagnosis and prophylaxis.

BACKGROUND OF THE INVENTION

Feline infectious peritonitis is a disease of cats characterized by the formation of pyogranulomatous lesions in various organs including kidney, liver and CNS (the non-effusive or "dry" form), or the development of fibrinous peritonitis and/or pleuritis (the effusive or "wet" form), or combinations of both characteristics (August, (1984) *Vet Clin North Am: Anim Pract* 14(5):975–984; Barlough and Stoddart (1986) in Contemporary Issues in Small Animal Practice Vol. 3 Infectious Diseases (F. W. Scott, ed.) Churchill Livingstone, New York, p. 93–108). Although its pathogenesis is still poorly understood, the disease appears to be an immunologically related one, with the primary lesion being vasculitis and perivasculitis resulting from the deposition of Arthus-like immune complexes within blood vessels.

Feline infectious peritonitis virus (FIPV) is the etiologic agent of FIP. FIPV viral antigen, IgG, and the third component of complement (C3) have been demonstrated in FIP lesions by immunofluorescence and a persistent FIPV infection is established in macrophages and cells of the regiculoendothelial system in infected cats. A more fulminating form of FIP is produced when kittens with FIPV antibody are challenged with virulent FIPV than when seronegative kittens are challenged.

FIPV is a single-stranded RNA virus (coronavirus family) whose genome is positive in polarity. From the RNA genome, a nested-set of 7–9 mRNAs are produced all terminating at the 3' end of the genome. The major structural proteins encoded by the virus include a nonglycosylated nucleocapsid (N) at 45 kD, a 26 kD envelope glycoprotein (E1), and a 210 kD glycoprotein which constitutes the surface peplomer (E2). In addition, there are open reading frames which, by analogy to other coronaviruses, encode nonstructural proteins (NS1 and NS2) that are expressed in FIPV-infected cells but which are not incorporated into FIPV virions.

Three kinds of prototype vaccines have been developed. The first involves the use of antigenically related (but avirulent in cats) corona viruses as live vaccines to stimulate neutralizing antibody titers. These include transmissible gastroenteritis virus (TGEV) of pigs, and canine coronavirus (CCV) of dogs. Results of these studies showed no protection, with little or no sensitization (Barlough et al., (1984) *Lab Anim Sci* 34(6):592–597; Woods and Pedersen, (1979) *Vet Microbiol* 4:11–16).

The second prototype involves the use of live, homologous FIP viruses (Pedersen and Black, (1983) *Am J Vet Res* 44(2):229–234; Pedersen and Floyd, (1985) *Compendium on Continuing Education for the Practicing Veterinarian* 7:1001–1011). Results indicate no protection, and in most cases, the cats are sensitized so that subsequent challenge with virulent virus resulted in enhanced FIP.

The third prototype, disclosed in PCT WO 87/04624, involves the use of an attenuated FIP virus of a specific strain (79-1146) which is claimed to protect and not cause sensitization when used as a live vaccine.

While different approaches have been attempted, the development of an efficacious vaccine against FIP has been elusive. To date, the only FIPV structural protein fully characterized is the E2, or peplomer glycoprotein. The cDNA sequence encoding E2 has been cloned and is provided in DeGroot et al., (1987) *J Gen Virol* 68:2639–2646; EP 264,979 also discloses the cloning of the E2 cDNA sequence and alleges its utility as a vaccine against FIP.

SUMMARY OF THE INVENTION

The invention provides the tools for synthesis and manipulation of the structural and nonstructural proteins of feline infectious peritonitis virus (FIPV). These proteins are useful in diagnosing an animal's exposure to FIPV or susceptibility to FIPV and also as subunit vaccines.

In one aspect, the invention relates to recombinant nucleic acid sequences which encode the structural and non-structural proteins of FIPV. In particular, these include the sequences for N, E1, NS1 and NS2 and biological derivatives thereof. In other aspects, the invention relates to recombinant vectors bearing these nucleic acid sequences which can be used to transform cells, and to the recombinant proteins produced by these transformed cells. Yet further aspects relate to methods of producing these FIPV proteins using recombinant techniques.

BRIEF DESCRIPTION OF THE DRAWINGS

FIGS. 1A, 1B, 1C, and 1D provide (SEQ ID NO: 7) provides the nucleotide and deduced amino acid sequences for the NS2, E1, N and NS1 polypeptides. The specific DNA sequences of the genes encoding the various proteins are as follows: NS2=nucleotides 641-853; E1=nucleotides 1954-2739; N=nucleotides 2755–3885; and NS1=nucleotides 3893–4195.

FIGS. 2A, 2B, and 2C illustrate the co-insertion vectors shown as generic vector pSC11 and pUV1 respectively.

MODES OF CARRYING OUT THE INVENTION

A. Definitions

As used herein, the term "FIPV protein" or "FIPV polypeptide" refers to structural proteins of the FIPV virion which include a 45K nucleocapsid protein (N), a 25K to 35K transmembrane glycoprotein (E1) and a 210K peplomer glycoprotein (E2); non-structural proteins predicted by open reading frames in the FIPV genome analogous to those encoded by other corona viruses, which include the proteins designated herein as NS1 and NS2 encoded by the DNA sequence provided in FIG. 1; and immunogenic fragments both recombinant and synthetic of the above-described viral proteins. The term "FIPV gene" is defined as the nucleic acid sequence encoding an FIPV protein. The terms are not limited to any subgroup or strain.

"Biological derivatives" includes mutants of structural and nonstructural proteins of FIPV which are at least 95% homologous to a structural or nonstructural protein of FIPV and recombinant or synthetic peptides encompassing immunological regions of FIPV as evidenced by their reactivity with FIPV antisera.

"Operably linked" refers to a juxtaposition wherein the components are configured so as to perform their usual function. Thus, control sequences or promoters operably linked to a coding sequence are capable of effecting the expression of the coding sequence.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and,optionally, transcription termination signals. Additional factors necessary or helpful in effecting expression may also be identified. As used herein, "control sequences" simply refers to whatever DNA sequence may be required to effect expression in the particular host used.

As used herein, the term "insertion vector" includes plasmids, cosmids or phages capable of mediating homologous recombination into a viral genome such that the heterologous nucleic acid sequence is stably carried by the resulting recombinant virus. In one embodiment of the invention plasmids constructed from vaccinia virus DNA are employed.

The term "expression vector" includes plasmids, cosmids or phages capable of synthesizing a protein encoded by the respective recombinant gene carried by said vector. Such vectors are independently replicated in or capable of integration into the chromosome of an appropriate host cell for expression of the desired protein.

B. Cloning of FIPV Genes

The FIPV structural and non-structural genes may be synthetic or natural, or combinations thereof. A natural FIPV gene (or portion thereof) may be obtained by preparing a FIPV cDNA or genomic library and screening for the presence of the viral genes. Preparation of cDNA libraries from a messenger RNA population is well known and described fully in Huynh et al. (1984) in DNA Cloning, Vol. 1: A Practical Approach (D. Glover, ed.), pp. 49–78, IRL Press, Oxford. Generally, if the library is to be screened by hybridization with a nucleotide probe, any insertion vector is appropriate but lambda-gt10 is preferred as it permits direct selection against nonrecombinant phages. If the library is to be screened by use of antibody probes, the most commonly used expression vector is lambda-gt11, in which the cloned coding sequences are fused to coding sequences for beta-galactosidase.

Screening may be accomplished using labeled DNA probes specific for the polypeptide or using antibodies for the gene product. Both methods are conventional and well described in the literature. Suitable antibodies may be prepared from purified FIPV. Suitable DNA probes may be obtained based on the amino acid sequence of the FIPV E2 structural protein, or based on the nucleotide sequences for the E1, N, NS1 and NS2 polypeptides as exemplified in FIG. 1 and in the Experimental section hereinafter.

When preparing a synthetic nucleotide sequence, it may be desirable to modify the natural nucleotide sequence. For example, it will often be preferred to use codons which are preferentially recognized by the desired host. In some instances, it may be desirable to further alter the nucleotide sequence to create or remove restriction sites to, for example, enhance insertion of the gene sequence into convenient expression vectors or to substitute one or more amino acids in the resulting polypeptide to increase stability.

Synthetic oligonucleotides are prepared by either the phosphotriester method as described by Edge et al., Nature (supra) and Duckworth et al., (1981) Nucleic Acids Res 9:1691 or the phosphoramidite method as described by Beaucage and Caruthers, (1981) Tet Letts 22:1859 and Matteucci and Caruthers, (1981) J Am Chem Soc 103:3185, and can be prepared using commercially available automated oligonucleotide synthesizers.

C. Recombinant Virus Vaccines

Moss et al., ((1983) Methods in Gene Amplification, Vol. 3, Elsevier-North Holland, p. 202–213; (1984) J Virol 49:857–864) describe the insertion of heterologous genes into the genome of vaccinia virus. These genes are then expressed during viral replication within the host resulting in an immune response to these gene products, as well as to vaccinia. Using this strategy, significant immunological response to and/or protection against challenge from a variety of pathogens, including influenza (Smith et al., (1983) Proc Natl Acad Sci, USA 80:7155–7159; Bennink et al., (1984) Nature 311:578), herpes simplex (Cremer et al., (1985) Science 228:737–740), hepatitis B (Moss et al., (1984) Nature 311:67–69), and Plasmodium knowlesi (Smith et al. , (1984) Science 224:397–399), has been demonstrated.

The technique involves construction of a plasmid insertion vector containing the heterologous FIPV gene downstream from a vaccinia viral promoter all of which is inserted into the vaccinia thymidine kinase (tk) gene within the insertion vector. Cotransfection of vaccinia DNA and the insertion vector into vaccinia virus-infected cells allows for homologous recombination between the TK sequences in the viral DNA and the plasmid, resulting in the insertion of the heterologous FIPV gene into the vaccinia genome and interruption of the viral tk gene. Recombinant viruses can be easily selected by virtue of their tk⁻ phenotype.

D. Vaccinia Viral Vectors

The coding sequences for the FIPV proteins can be inserted into vaccinia virus plasmid insertion vectors for the purpose of generating recombinant vaccinia viruses. The FIPV-vaccinia recombinants can then be used for (1) expression and analysis of the respective FIPV proteins, (2) production of FIPV antibodies, (3) production of FIPV proteins in tissue culture for use as killed or inactivated immunogens in cats, or (4) use as living virus immunogens in cats.

In the present invention, plasmids pSC11 and pUV1 were used for the expression of the FIPV proteins and generation of FIPV-vaccinia recombinants. Samples of E. coli transformed with plasmids containing the coding sequences for NS1, NS2, E1 and N were deposited under the Budapest Treaty at the American Type Culture Collection (ATCC), 12301 Parklawn Drive, Rockville, Md. on 30 Aug. 1988. The names of the three plasmids are p64-FIPV6, pBR329-FIPV9, and pBR329-E2#2, which were assigned ATCC numbers 67784, 67783, and 67782, respectively. In FIG. 1, the plasmids encompass the following nucleotide sequences: pBR329-E2#2 (1-2784); pBR329-FIPV9 (2049–3896); and FIPV6 (3673–5130).

Figure 2B:
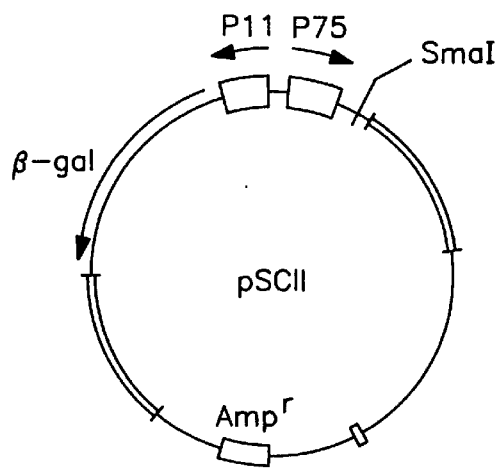
Figure 2C:
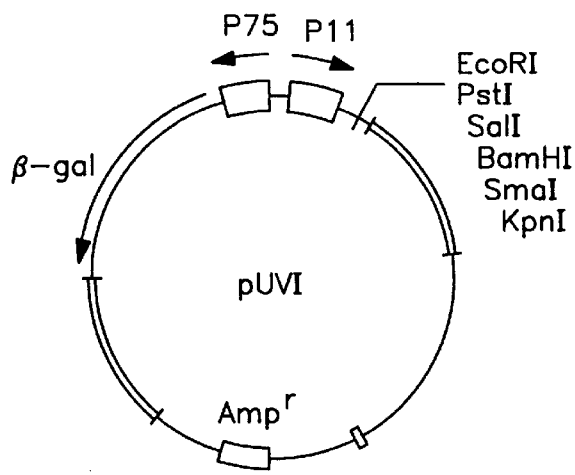

The two vaccinia virus insertion vectors, pSC11 (Chakrabarti et al., Mol Cell Biol (1985) 5:3403–3409) and pUV1 Falkner, F. G. et al., Nucleic Acids Research (1987) 15:7192) were used to generate FIPV recombinants. Both vectors are of the co-insertion variety illustrated in FIG. 2A. These vectors contain two vaccinia virus promoters. One promoter (P1) is used to drive the expression of a selectable marker gene (in this case, betagalactosidase). The other promoter (P2) is used to drive expression of the heterologous FIPV cDNA insert. Both are flanked by vaccinia virus DNA (an interrupted thymidine kinase [tk] gene) which facilitates homologous recombination into a wild-type vaccinia virus genome and provides a selection mechanism (generation of tk minus viruses). The pSC11 vector (FIG. 2B) utilizes a vaccinia early-late promoter (P7.5) to drive heterologous gene expression and has a single SmaI cloning site. The pUV1 vector (FIG. 2C) utilizes a vaccinia late promoter (P11)(SEQ ID NO:6) to drive heterologous gene expression and is designed for the expression of fusion proteins behind the ATG of the P11 late gene. In all cases, FIPV-pUV1 constructs were made using the most 5' (after the ATG) cloning site (EcoRI) in order to avoid introduction of additional amino terminal amino acids into the native FIPV protein sequence.

E. Recombinant Expression Vectors and Hosts

It will also be understood by those skilled in the art that both procaryotic and eucaryotic systems may be used to express the FIPV genes described herein. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar et al., (1977) *Gene* 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., (1977) *Nature* 198:1056), the tryptophan (trp) promoter system (Goeddel et al., (1980) *Nucleic Acids Res* 8:4057), the lambda-derived $P_L$ promoter (Shimatake et al., (1981) *Nature* 292:128) and N-gene ribosome binding site, and the trp-lac (trc) promoter system (Amann and Brosius, (1985) *Gene* 40:183).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2 micron origin of replication of Broach, (1983) *Meth Enz* 101:307, or other yeast compatible origins of replication (see, for examples Stinchcomb et al., (1979) *Nature* 282:39, Tschumper et al., (1980) *Gene* 10:157 al., (1983) *Meth Enz* 101:300) may be used. Control sequences for yeast vectors include promoters for the synthesis of glycolytic enzymes (Hess et al., (1968) *J Adv Enzyme Reg* 7:149; Holland et al., (1978) *Biochemistry* 17:4900). Additional promoters known in the art include the promoter for 3-phosphoglycerate kinase (Hitzeman et al., (1980) *J Biol Chem* 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel et al., U.S. Pat. No. 4,399,216. These systems have the additional advantage of the ability to splice out introns and thus can be used directly to express genomic fragments. Useful host cell lines include VERO, HeLa, baby hamster kidney (BHK), CV-1, COS, MDCK, NIH 3T3, L, and Chinese hamster ovary (CHO) cells. Useful feline host cells include Crandall Feline Kidney Cells (CRFK) and Fetal Cat Whole Fetus (FCWF). Expression vectors for such cells ordinarily include promoters and control sequences compatible with mammalian cells such as, for example, the commonly used early and late promoters from Simian Virus 40 (SV40) (Fiers et al., (1978) *Nature* 273:113), or other viral promoters such as those derived from polyoma, herpes virus, Adenovirus 2, feline retroviral LTR from feline leukemia virus, bovine papilloma virus, or avian sarcoma viruses. The controllable promoter, hMTII (Karin et al., (1987) *Nature* 299:797–802) may also be used. General aspects of mammalian cell host system transformations have been described by Axel, *supra*.

Insect expression systems may also be employed to express the FIPV genes. For example, the baculovirus polyhedrin gene has been employed for high-level expression of heterologous proteins (Smith et al., (1983) *Mol Cell Biol* 3(12):2156–2165; Summers et al., "Genetic Engineering of the Genome of the *Autographa Californica* Nuclear Polyhedrosis Virus", Banbury Report: Genetically Altered Viruses in the Environment, 22:319–339, Cold Spring Harbor Laboratory, 1985).

F. Generation of Stably Transfected Cell Lines

The FIPV cDNA clones expressed in vaccinia can also be used to generate stably transfected cell lines expressing the FIPV subunit protein. In general, these cell lines are generated by first constructing one of two expression plasmids. In both expression plasmids, the selectable marker is provided by a G418 neomycin expression cassette (neo) consisting of the SV40 early promoter, the bacterial kanamycin-resistance gene also containing its own promoter, the SV40 intervening sequence, and the SV40 polyadenylation site from the early region. In the first expression plasmid, the FIPV cDNA cloning site is flanked at the 5' end by the human metallothionine gene promoter, pMtIIa, modified with an SV40 enhancer, and at the 3' end by the SV40 polyadenylation site from the early region. In the second expression construct, the FIPV cDNA cloning site is flanked at the 5' end by a feline leukemia virus (FeLV) long terminal repeat sequence (LTR) providing promoter functions which are particularly functional in feline cells, and at the 3' end by a sequence encoding a useful polyadenylation site, such as that of the SV40 early region or the beta-actin gene.

Each of the vectors described above can be transformed into a mammalian cell line such as, but not limited to, those described in the following examples by either calcium phosphate-DNA coprecipitation or electroporation. A day later, the cells are subjected to 1 mg/ml G418 to provide pools of G418-resistant colonies. Successful transformants, also having a stable inheritance of the FIPV cDNA contained in the expression construct, are then plated at low density for purification of clonal isolates. Clonal isolates are then analyzed for maximum production of the FIPV protein of interest and high-producing clones are expanded to serve as vaccine seeds.

G. Diagnostic Uses

The FIPV proteins or an immunogenic peptide segment derived from the protein can be used as diagnostic reagents in determining whether a cat has been previously exposed to FIPV and allows for a means to determine a cat's susceptibility to the disease. This can be done by assaying a number of cat biological samples. First, the cat's serum can be assayed for the presence of FIPV antibodies. Second, cell lysates or whole fixed cells from a cat can be assayed to determine if an FIPV protein is being expressed. In the first case, an FIPV protein is the diagnostic tool. In the second case, an antibody directed against an FIPV protein is the diagnostic tool.

Standard protocols can be employed for preparing antibodies directed against the FIPV proteins of the invention. Techniques for preparing both polyclonal and monoclonal antibodies are well known in the art. Briefly, polyclonal antibodies are prepared by injecting FIPV protein with an adjuvant into an animal such as rabbits or mice. The FIPV protein may need to be conjugated to a carrier protein such as bovine serum albumin or keyhole limpet hemacyanin using a chemical process which employs carbodiimide, glutaraldehyde, or other cross-linking agents. Alternatively, the protein may be administered without being conjugated to a carrier protein. Vaccinia recombinants which are expressing FIPV proteins may also be used to prepare antibodies. The animal is boosted several weeks after the initial immunization. Ten days to two weeks later the animals are bled and antiserum is collected and analyzed for titer.

Monoclonal antibodies are commonly prepared by fusing, under appropriate conditions, B-lymphocytes of an animal which is making polyclonal antibodies with an immortalizing myeloma cell line. The B-lymphocytes can be spleen cells or peripheral blood lymphocytes. Techniques for fusion are also well known in the art, and in general, involve mixing the cells with a fusing agent such as polyethylene glycol. Successful hybridoma formation is assessed and selected by standard procedures such as, for example, HAT medium. From among successful hybridomas, those secreting the desired antibody are screened by assaying the culture medium for their presence.

Standard immunological techniques such as ELISA (enzyme-linked immunoassay), RIA (radioimmunoassay), IFA (immunofluorescence assay) and Western blot analysis, which are well known in the art, can be employed for diagnostic screening for FIPV. A vast literature now exists with respect to various modifications of the basic assay principle, which is simply that there must be a specific association between target analyte and antibody, which association is detectable qualitatively and/or quantitatively. Fluorescent, enzymatic, or radioactive labels are generally used. One typical arrangement utilizes competition, between labeled antigen (e.g. FIPV protein) and the analyte, for the antibody, followed by physical separation of bound and unbound fractions. Analyte competes for the binding of the labeled antigen; hence more label will remain in the unbound fraction when larger amounts of analyte are present. In this competitive-binding type assay, the sample is incubated with a known titer of labeled FIPV protein and FIPV protein antibody. Antibody-protein complex is then separated from uncomplexed reagents using known techniques and the amount of label in the complexed material is measured, e.g. by gamma counting in the case of radioimmunoassay or photometrically in the case of enzyme immunoassay. The amount of FIPV protein in the sample, if any, is determined by comparing the measured amount of label with a standard curve. Other embodiments of this basic principle include use of labeled antibodies per se, sandwich assays involving a three-way complex between analyte, anti-analyte antibody, and anti-antibody wherein one of the components contains a label, and separation of bound and unbound fractions using an immunosorbent. Agglutination assays which result in visible precipitates are also available. Limet et al., (1982) *J Clin Chem Clin Biochem* 20:142–147.

In addition, the antisera may be tested for the ability to neutralize virus infectivity. Antisera raised against FIPV open reading frame products or against genes of unknown function may be used to identify potential targets of neutralizing immune responses. The neutralizing response can be assayed by injecting such antisera into an animal subject, followed by challenge with FIPV and observing the response.

The proteins or nucleotide probes also provide the diagnostic tools to differentiate a naturally infected FIPV-diseased cat from one that has been immunized with a subunit vaccine and therefore would not produce antisera against all FIPV proteins.

H. Administration and Formulations

Infectious recombinant viruses or cell lines created by the methods of the instant invention are useful as FIPV vaccines. In particular, we have demonstrated that innoculation of cats with a live virus comprising vaccinia virus containing a functional DNA insert for the N protein of FIPV has an immunizing effect against subsequent challenge with FIPV. It is contemplated within the scope of the invention to employ a recombinant virus or cell line expressing one or both of the nonstructural proteins, NS1 and NS2, as a vaccine to immunize cats against FIPV. A recombinant virus or cell line expressing or comprising any combination of the N, E1, E2, NS1 and NS2 proteins is also contemplated for use as a FIPV vaccine. It is further contemplated that the FIPV vaccines of the invention include immunogenic peptide segments of the aforementioned proteins or combination of proteins, or biological derivatives thereof as defined above.

Vaccines can be administered by a variety of routes, for example, parenterally (subcutaneously, intradermally, intraperitoneally, intramuscularly, intrasternally, among others), by intranasal aerosol, or orally. The dose and dosage regimen used in the vaccination may vary depending on the age and weight of the animal, the mode of administration, and the presence of adjuvants in the formulation. Individual doses will usually be in the range of 100 ng to 1 mg of immunogen. In addition, one or more of the FIPV proteins may be combined in a single formulation for administration. As indicated, the vaccine formulations are preferably used to prime the, immune response and are followed by injection with killed virus or subinfectious amounts of live virus. The vaccination will typically be followed by booster inoculations periodically through the first year of life and beyond. As used herein, the term "immunogenic amount" is intended to encompass such doses.

The following examples are intended to further illustrate the invention and are not intended to limit the invention in any manner.

EXAMPLES

Most to the techniques which are used to transform cells, construct vectors, extract messenger RNA, prepare cDNA libraries, perform immunoassays, and the like are widely practiced in the art, and most practitioners are familiar with the standard resource materials which describe specific conditions and procedures. The examples are written in observation of such knowledge and incorporate by reference procedures considered conventional in the art.

Example 1

Cloning of FIPV cDNAs

A. Synthesis of cDNA Libraries

Two cDNA libraries were constructed from different viral sources. The first library used poly(A)+RNA from cells infected with Fort Dodge Type II FIPV (Black (May 1980) *Vet Med/Small Animal Clin*, pp. 811–814) while the second library used cells infected with the 79–1146 isolate of FIPV as the source of the poly(A)+RNA. The double-stranded cDNA was synthesized by a modification of the RNAse H procedure (D'Alessio et al, (1987) *Focus* 9(1):1–4). Generally, the modification involves the synthesis of first and second strand cDNA in a single tube reaction.

First strand synthesis was conducted using 10 ul of 5× reaction buffer (250 mM Tris-HCl, pH 8.3; 375 mM KCl; 50 mM DTT; and 15 mM $MgCl_2$), 2.5 ul of 10 mM dNTP, 5 ul of 1 mg/ml oligo-dT, 29 ul of RNA+$H_2O$, 2.5 ul of 400 U/ul Moloney virus reverse transcriptase (BRL) and 1 ul of 1 U/ul RNAsin (BRL). For the first cDNA library 8.4 ug of poly (A)+ RNA was used as template and 6.5 ug of poly(A)+ RNA was used to generate the second library. The RNA was heat-treated for 3 min at 68° C. prior to its addition to the reaction mixture. The reaction mixture was incubated for 1 hr at 37° C.

For second strand synthesis 45 ul of the above mRNA:cDNA hybrid reaction mixture was added directly to 64 ul of 5× second strand buffer (95 mM Tris-HCl, pH 8.3; 455 mM KCl; 25 mM $MgCl_2$; and 20 mM DTT), 6.4 ul of 10 mM dNTP, 10 ul of $^{32}$P-dCTP, 168 ul of $H_2O$, 16 ul of 1 mg/ml BSA, 8 ul of 10 U/ul DNA polymerase I (NEB) and 2 ul of 2 U/ul RNAse H (BRL). This reaction was incubated for 2 hr at 16° C. and stopped by addition of EDTA to 5 mM. The cDNA was extracted once in phenol/$CHCl_3$, followed by extraction in $CHCl_3$ and ethanol precipitated.

Next, the cDNA was methylated, blunt-ended, and EcoRI linkers were added according to the procedure of Maniatis et al., *Molecular Cloning: A Laboratory Manual* (1982) Cold Spring Harbor press. Following digestion with EcoRI restriction enzyme the cDNA was ligated to EcoRI-digested and phosphatased lambda gt10 arms (Huynh et al., (1984) In *DNA Cloning*, Vol 1: A Practical Approach (D. Glover, ed.) pp. 49–78, IRL Press, Oxford). The ligation mixture was packaged into infectious phage particles (Stratagene) and the packaged phage were grown on *E. coli* (C600 hfl A).

B. Isolation of NS1, N and E1 Genes

1. Probe Synthesis

The first cDNA library was screened with a "subtracted probe." This probe was generated by synthesizing first strand cDNA from RNA derived from FIPV infected cells, removing the template RNA by NaOH treatment, then hybridizing the cDNA with excess RNA prepared from uninfected cells. Following this hybridization, the cDNA was added to filters without boiling of the probe. Only those cDNAs which are viral specific, and thus not bound to the excess RNA, are available for binding to plaques on filters.

Probe cDNA was synthesized by mixing 10 ul of 5× reaction buffer, 2.5 ul of 10 mM dATP, TTP, dGTP, 10 mM $MgCl_2$, 5 ul $^{32}$P-dCTP, 5 ul RNAsin, and 2.5 ul Moloney virus reverse transcriptase (400 units/ul; from BRL). To the above mixture was added 24 ul of RNA (0.5 ug) in water and 5 ul of random primers (50 mg/ml in $H_2O$; from Pharmacia) which had been heated for 15 min at 65° C. The reaction mixture was run for 1 hr at 37° C. and stopped by addition of EDTA to 10 mM. NaOH to 0.2M was added and the reaction incubated at 65° C. for 1 hr to hydrolyze the RNA template. The reaction was neutralized by adding Tris-HCl, pH 8 to 0.2M and the pH adjusted to 7 through addition of 1M HCl.

Next, 10 ug of yeast tRNA was added and the cDNA precipitated using $NH_4QAc$. The cDNA was solubilized in water to which the "subtraction RNA" and vanadyl ribonucleoside complex (VRC from BRL) were added to 10 mM final concentration. This solution was heated at 65° C. for 5 min and then added to the hybridization solution (75 ul of 20× SSC, 30 ul of 0.5M HEPES, pH 6.9, 120 ul formamide, 15 ul of 200 mM VRC, and 60 ul of subtraction RNA, cDNA and $H_2O$). This latter solution was incubated overnight at 42° C. and then the cDNA was added to filters.

Filters were hybridized in 5× SSPE, 40% formamide, 0.5% nonfat dry milk, 0.1% SDS and 10 ug/ml tRNA overnight at 37° C., then washed at 50° C. in 0.2× SSC before exposure to film.

2. Analysis of cDNAs

Eight clones that were identified with the subtracted probe were plaque-purified by standard procedures. Phage DNA was prepared and EcoRI digestions were performed. Two clones containing the largest inserts were chosen for further study. FIPV #6 cDNA is approximately 1.6 kb in length and FIPV #9 cDNA is approximately 3.1 kb.

Initial sequence from clone #6 exhibited homology to TGEV sequence. Clone #9 overlapped and extended this sequence, and was used to derive the entire sequence for the NS1 and N genes of FIPV. The sequences of these genes is provided in FIG. 1. Since clone #9 did not completely extend to the 5' end of the E1 gene, the first cDNA library was screened with an oligonucleotide (5'-TCGTAAGCGCTAGAACAA-3') (SEQ ID NO:7) derived from the amino terminal sequence of clone #9. The oligonucleotide was kinased using $^{32}$ P-ATP following standard procedures and hybridization performed in 6× SSPE, 1 mg/ml heparin, 0.5% nonfat dry milk and 0.1% SDS. Filters were hybridized at 37° C. overnight, then washed at 50° C. in 6× SSC before exposure to film.

A clone was isolated (#3a-2) which extended the 5' end of the E1 sequence another 200 bp. The completed E1 sequence was thus obtained. FIPV clones #9 and #3a-2 were used to generate a fragment encoding the entire sequence of the E1 and N genes. Clone #3a-2 was digested with EcoRI and SspI restriction enzymes under standard conditions and an ~200 bp EcoRI-SspI fragment was isolated. Clone #9 was digested under similar conditions using EcoRI, SspI and SphI restriction enzymes. An ~1.7 kb SspI-SphI fragment was isolated from the digestion products and was ligated to the ~200 bp EcoRI-SspI fragment isolated from clone #3a-2. This ligated EcoRI-SphI fragment containing the entire coding sequences for the E1 and N genes was subcloned into EcoRI- and SphI-digested pUC18, the resulting clone being designated pUC18:E1-N. Standard procedures for isolation of fragments, ligation, and subcloning into plasmids were followed throughout this example. The correct E1-N construct was verified by growing mini-prepped DNA and performing restriction enzyme digests on the resulting plasmid DNA.

Example 2

Isolation of E2 and NS2 cDNAs

The second library was used to isolate a cDNA sequence encoding E2. The oligonucleotide probes disclosed in Table 1 below were designed from the published sequence to E2 (deGroot et al., supra).

TABLE 1

E2 Oligos

| Oligo No. | Nucleotide Sequence |
|---|---|
| 7 | AACTGTGTGGTATGAACA (SEQ ID NO: 8) |
| 8 | TACGTTAACTTGTATGCA (SEQ ID NO: 9) |
| 9 | AGAGCAGTTGTACCACAC (SEQ ID NO: 10) |
| 10 | ATTATCAGACGGTACACC (SEQ ID NO 11) |
| 11 | GTAATCTGTACAGGAGTC (SEQ ID NO 12) |
| 12 | CAGCCTATCAACTTGTGC (SEQ ID NO 13) |
| 13 | TTGTCTGGTTAGAGTCTG (SEQ ID NO 14) |
| 14 | TCTAGGCTGATACATAGT (SEQ ID NO 15) |

Hybridization conditions were as described for the oligonucleotide screening. Two cDNA clones, each containing a cDNA insert of 6 kb in length, were isolated and subcloned into pBR329; these were designated p329(88):E2#1 and p329(88):E2#2. The latter plasmid is also designated pBR329-E2#2. From a combination of nucleotide sequences and Southern blotting experiments, the clones start at nucleotide 463 of the published E2 sequence, extend to the end of E2, and then continue into NS2 and E1

Example 3

Construction of Vaccinia Virus Insertion Vectors

Recombinant vaccinia viruses bearing FIPV cDNAs encoding each of five FIPV proteins were generated by standard methods as reviewed by Mackett and Smith [(1986) *J Gen Virol* 67:2067–2082], which is incorporated herein by reference. One of two (or both) co-insertion vectors as illustrated in FIG. 2 were used for each cDNA. The pSC11 vector has a single blunt-end cloning site (SmaI) with the ATG supplied by the cDNA insert. The pUV1 vector provides multiple cloning sites, all of which occur after the vaccinia P11 promoter ATG. Therefore, all pUV1-FIPV constructs require that the FIPV coding sequences be placed in frame with the p11 ATG. Specifics for each construct are as follows:

pSC11-NS2

The NS2-encoding sequence (n.t. 641-653) was isolated from pBR329-E2#2 as a blunt-ended XmnI (n.t. 599)-PvuII (n.t. 2124) fragment-which was subcloned into the SmaI site of pSC11. The NS2 ATG at n.t. 641 is the first initiation codon encountered 3' to the cloning site.

pUV1-NS2

The NS2-encoding sequence was isolated from pBR329-E2#2 as a Tth111I (n.t. 648)-PvuII (n.t. 2124) fragment. The single base pair overhang at the Tth111I site was filled in with Klenow reagent. The pUV1 vector was prepared by EcoRI digestion followed by filling in with Klenow reagent. The blunted NS2 fragment was then subcloned into the blunted EcoRI site of pUV1 after the p11 ATG. This results in a change in the amino terminus of FIPV-NS2 from "met-asp-ile-val-lys. . ." (the first 5 residues of SEQ ID NO:2) to "met-asn-phe-val-lys. . ." (SEQ ID NO:16). The variant residues are underlined.

pSC11-E1

The E1-encoding sequence (n.t. 1954-2739) was isolated from pUC18:E1-N (see Example 1) as an EcoRI (n.t. 1921)-BalI (n.t. 2759) fragment with blunting of the EcoRI site with Klenow reagent. The EcoRI site is not present in the FIG. 1 sequence as it was a linker site present in one of the original lambda clones (#3a-2; see Example 1). The location of this site is indicated in FIG. 1 by "[EcoRI J]". The blunt EcoRI-BalI E1 fragment was subcloned into the SmaI site of pSC11. The E1 ATG at n.t. 1954 is the first initiation codon encountered 3' to the cloning site.

pSC11-N

The N-encoding sequence (n.t. 2755-3885) was isolated as a MluI (n.t. 2773)-SPhI (n.t. 3896) fragment from pUC18:E1-N. A SmaI-MluI linker was added at the 5' end providing a SmaI cloning site and restoring the N ATG and coding sequences which occur 5' to the MluI site. An SphI-SmaI linker was added to the 3' end. The resulting SmaI N fragment was subcloned into the SmaI site of pSC11.

pUV1-N

The N-encoding sequence was isolated as a BalI (n.t. 2759)-HindIII fragment from pUC18:E1-N. The HindIII site was supplied by the pUC18 polylinker region. The HindIII site was filled in with Klenow reagent. The resulting blunt-ended N fragment was subcloned into the blunted EcoRI site of pUV1after the p11 ATG. Due to this method of subcloning, the amino acid terminal N sequence is changed from "met-ala-thr-gln. . ." (First 4 residues of SEQ ID NO:4) to "met-asn-ser-thr-gln . . ." (SEQ ID NO:7). The variant or added residues are underlined.

pSC11-NS1

The NS1-encoding sequence (n.t. 3893-4195) was isolated from p64-FIPV6 as an SphI (n.t. 3896)-EcoRI (n.t. 5126) fragment. A linker was added at the SphI site which restored the NS1 ATG and supplied a 5' EcoRI cloning site. The 5' and 3' EcoRI sites were filled in with Klenow reagent and the blunt-ended N fragment was subcloned into the SmaI site of pSC11.

pUV1-NS1

The EcoRI NS1 fragment described above (after linker addition) was subcloned directly into the EcoRI site of pUV1. This results in a change of the amino terminal NS1 residues from "met-leu-val-phe. . . " (First 4 residues of SEQ ID NO:5) to "met-asn-ser-met-leu-val-phe. . ." (SEQ ID NO:18). The additional residues are underlined.

pUV1-E2Δ5'

The FIPV cDNA clone p329(88):E2#2 (see Example 2) contains 3893 nucleotides of E2 sequence encoding about 90% of the E2 protein to the carboxy terminus. The sequence begins at an EcoRI site located at n.t. 463 of the deGroot et al. sequence, supra. (The stop codon for the E2 protein occurs at n.t 572 in FIG. 1.) A pUV1 insertion plasmid construct was made by purifying a 3921 n.t. EcoRI-XmnI (n.t. 599 in FIG. 1) fragment containing the E2 sequences described above and subcloning the fragment into the EcoRI-SmaI sites in the pUV1 polylinker (see FIG. 2C). This places E2 protein sequences in frame with the p11 ATG such that the first residues are "met-asn-ser . . . ". The correct E2 sequence (deGroot et al.) begins with the "asn-ser. . . " residues.

pSC11-E2

The 5' E2 cDNA sequence is generated from FIPV 1146 RNA (Pedersen et al., (1984) *Am J Vet Res* 45(12):2580–2585) utilizing the polymerase chain reaction [Saki et al., (1988) *Science* 239:487–491 and Stoflet et al., (1988) *Science* 239:491–494]. A blunt cloning site is constructed 5' to the natural E2 ATG such that the entire E2 fragment could be blunted into the SmaI site of pSC11 using the 5' blunt site and the 3' XmnI site described above in the pUV1-E2 5' construction example.

pUV1-E2

Using site-directed mutagenesis, an EcoRI site is inserted after the native E2 ATG such that the 5' E2 sequences to n.t. 463 could be isolated as an EcoRI fragment which is then inserted into the EcoRI site of the construct pUV1-E2Δ5'.

The resulting construct contains the complete E2 sequence after the p11 initiation codon. The amino terminal E2 sequences "met-ile-val-leu-val . . . " (SEQ ID NO:19) become "met-asn-ser-leu-val . . . " (SEQ ID NO:20). Variant residues are underlined.

Example 4

Generation of Vaccinia Virus Recombinants

The vaccinia insertion vectors described in Example 3 were used to generate FIPV-vaccinia recombinant viruses as follows.

Preparation of FIPV-Vaccinia Virus Recombinants

Confluent monolayers of CV-1 cells in 60 mm dishes were infected with vaccinia virus (Wyeth strain) at an multiplicity of infection (moi) of 0.05 pfu/cell. At 2 hr post-infection, the cells were transfected with a calcium phosphate precipitate of 10 ug insertion plasmid DNA and 0.5 ug wild-type vaccinia virus DNA. Cells were fed with complete medium and incubated at 37° C. for two days. Monolayers were collected and $TK^{31}$ vaccinia viruses were selected on $TK^-143$ cells in the presence of 5-bromodeoxyuridine (BudR) at 25 ug/ml. At 48 hr after infection, monolayers were overlaid with 1% agarose containing 300 ug/ml 5-bromo-4-chloro-3-indolyl-B-D-galactopyranoside (Xgal). At 4–6 hr, blue plaques were picked and further purified by two additional rounds of plaque purification in the presence of BudR and Xgal.

Stocks of the FIPV-vaccinia recombinant viruses were prepared in $TK^-143$, CV-1, or VERO cells. Recombinant viral DNA was prepared from each stock and was shown by Southern blot analysis to contain the appropriate FIPV cDNA insert and to be free of contamination with wild-type or spontaneous $TK^-$ vaccinia.

Identification of FIPV-specific Polypeptides Produced by Vaccinia Virus Recombinants in Tissue Culture A cat ascites reagent had been previously identified which specifically immunoprecipitated FIPV structural proteins (N, E1, and E2) from FIPV Type I and FIPV Type II infected FCWF or CRFK tissue culture cells. When CV-1 cells are infected with the vaccinia-FIPV E1, N, or E2 recombinants at an moi of 5–10 and radiolabeled with [$^{35}$S] methionine, infected cell lysates can be prepared and FIPV-specific polypeptides of the predicted molecular weights can be immunoprecipitated with the cat ascites reagent (by PAGE analysis). In the case of the NS1 and NS2 recombinants, no immunological reagent was available which recognized these previously unidentified FIPV-encoded proteins. However, antisera raised in rabbits to the NS1 and NS2 recombinants can be used to specifically immunoprecipitate novel polypeptides from FIPV virus infected cells and not from mock infected cells, thus proving that the nonstructural recombinants are making FIPV encoded proteins.

The recombinant virus stocks described above are used either as living immunogens or are used to infect monolayers of susceptible cells in which the FIPV subunit protein is subsequently expressed. Monolayers containing the vaccinia expressed recombinant FIPV protein are then harvested and inactivated for use as a killed immunogen.

Example 5

Preparation of Proteins
Method of Vaccinia Virus Propagation

One hundred percent confluent monolayers of mammalian cell cultures such as, but not limited to, Crandall Feline Kidney Cells (CRFK), Wood's Feline Cell Line (FC), Fetal Cat Whole Fetus (FCWF), a Dog Kidney Cell Line (DK), Madin Darby Canine Kidney Cells (MDCK), Baby Hamster Kidney Cells (BHK), African Green Monkey Kidney Cells (VERO) are inoculated with FIPV-vaccinia recombinant viruses measured in Tissue Culture Infectious Dose ($TCID_{50}$) or Plaque Forming Units (pfu) in a virus to cell ratio of 1:10,000 to 1:10, preferably 1:5000 to 1:100, more preferably 1:1500 to 1:500. Optimally, at the time of inoculation, the cells should be present in the growth vessel in an amount sufficient to form a monolayer of cells of at least 100,000 to 1,000,000 cells per square centimeter ($cm^2$), preferably 150,000 to 500,000 cells/$cm^2$, within about 12–48 hr, preferably within 24 hr after cell inoculation. The virus is adsorbed on the cells for at least 60 min but less than 300 min, preferably between 90 and 240 min at 28° C. to 38° C. before refeeding the vessel with maintenance medium.

Harvestable virus titers of at least 1000 particles but usually not more than 500,000,000 and usually 5,000,000 particles as measured by the $TCID_{50}$ and noted by >80% cytopathic effect (CPE) in the cell culture can be obtained within 24 to 96 hr after inoculation. The cell monolayer is removed by multiple freeze-thawings and sonicated, then either inactivated or stored frozen.

In a specific example, ten 850 cm square roller bottles or VERO cells were poured off and FIPV-Vaccinia seed titered at 5.2 log $TCID_{50}$ per ml was added to each roller bottle. Each roller bottle contained 150,000,000 confluent VERO cells, so the moi of virus to cell ratio was 1:100. The virus was adsorbed with 50 ml of MEM for 3 hr and then refer with maintenance MEM. The virus fluids were harvested at 72 hr after inoculation and produced a virus titer of 6.25 log $TCID_{50}$ per ml. After 40× PEG concentration (see below), the virus titered 8 log $TCID_{50}$ per ml. Virus preparations to be used as living immunogens may also be concentrated to achieve inoculation concentrations of $10^6$–$10^8$ pfu per dose. Such crude viral stocks may be used to directly immunize animals or stocks may be lyophilized and reconstituted in an appropriate diluent.

Virus preparations that are to be used as killed immunogens are inactivated, concentrated, and adjuvanted using standard protocols.

Method of Stably Transfected Cell Line Propagation

Stably transfected cell lines which constitutively express FIPV protein are grown to 100% confluency in 850 $cm^2$ roller bottles. After cells have reached maximum density, they are harvested by freeze-thawing three times and may be concentrated as described for virus fluids. The cell line fluids are inactivated, concentrated, and adjuvanted using standard protocols.

Binary Ethyleneimine (BEI) Inactivation of Virus Fluids or Cell Line Fluids

Equal volumes of a 0.2 molar bromoethylamine hydrobromide solution and a 0.4 molar sodium hydroxide solution are mixed and incubated at about 37° C. for 60 min. The resulting cyclized inactivant is binary ethyleneimine (BEI) which is added to the virus fluids or cell line fluids at 0.5 to 4%, volume to volume. The inactivating virus or cell line fluids are held from 4°–37° C. for 24 to 72 hr under periodic agitation.

The activated virus or cell line fluids are passaged three times in cell culture and examined for specific virus growth to test for complete inactivation.

Concentration of Virus or Cell Line Fluids

The virus or cell line fluids may be concentrated from 2 to 50 times by any number of available techniques such as Amicon, Pellicon (Millipore) concentrating devices, precipitation techniques, such as ammonium chloride or polyethylene glycol, concentration with Carbowax liquid or wax in conjunction with dialysis tubing, or adjuvant concentration techniques, such as with aluminum phosphate. For the PEG concentration method 80 ml of 50% PEG is added to 1 liter of virus or cell line 15 fluids, then mixed overnight at 4° C. The next day the PEG-virus fluids are centrifuged at >2500 RPM, the supernatant is discarded, and the PEG-virus pellet is resuspended in the correct volume of media to achieve the desired concentration.

Adjuvanting Virus or Cell Line Fluids

The following adjuvants may be used separately or in combination with 2 or more adjuvants depending on interdermal induration reactions in animals and adjuvant mixing compatibility.

Ethylene maleic anhydride (EMA) prepared at a 1% weight to volume concentration in water is added to the inactivated virus or cell line fluids at 0.01% to 6% volume to volume [concentration separately or in combination with other adjuvants]. The pH of the resulting fluids is adjusted to 7.1 to 7.7 by addition of 1N sodium hydroxide.

Neocryl A640 is a trade name for a latex emulsion of a copolymer [A styrene and a mixture of acrylic acid and methacrylic acid]. Neocryl A640 is an uncoalesced aqueous acrylic copolymer with styrene, having pH 7.5, viscosity 100 cps (Brookfield 25° C.), weight per gallon is 8.6 lbs as supplied containing 40% solids by weight and 38% solids by volume. The numeral A640 denotes a grade thereof. Other useful Neocryl grades are 520, 625, and 966. The term "CSMA" will be used hereinafter to refer to a copolymer of styrene and a mixture of acrylic acid and methacrylic acid. CSMA prepared in a 50% volume per volume suspension in water is added to the inactivated virus or cell line fluids from 0.2 to 10% volume separately or in combination with other adjuvants. Usually there is no need for pH adjustment since the CSMA is a neutral pH.

Modern Veterinary Products (Omaha, Nebr.) Emulsigen adjuvant for small animals is an oil-in-water emulsion which is used separately or in combination with other adjuvants in a 1 to 20% volume to volume of virus or cell line fluids.

Avridine is used separately or in combination with other adjuvants at from 5 to 30 mg per dose. Avridine at 2.4 gm is dissolved in 18 ml of absolute ethyl alcohol, then 1.8 ml of Tween-80 is added and the mixture is passed through a 0.2 micron filter. Next 20.2 ml of Intralipid soy bean oil is aseptically added to the avridine. Seven to 50% of this adjuvant is then added volume to volume to the virus or cell line fluids.

Saponin is used separately or in combination with other adjuvants at from 0.01 mg to 5 mg per dose. Saponin is prepared at a 200 mg/ml concentration, filter sterilized and then added to the virus or cell line fluids at from 0.01 to 50% volume to volume.

Aluminum phosphate at from 0.01 to 5 mg per dose or aluminum hydroxide at from 0.5 to 20 mg per dose may also be used separately or in combination with other adjuvants.

Cell and Virus Growth Medium

In vaccine production cells were grown in minimal essential media (MEM) supplemented with vitamins, nonessential amino acids, sodium pyruvate, sodium bicarbonate and L-glutamine. Gentamicin at 30 ug/ml was added to the media as a preservative and up to 10% bovine serum was added for cell growth, up to 1% for maintenance medium.

Example 6

Cat Trials: Efficacy of vaccines

Efficacy or immunoprotection may be evaluated by observing the effects of a virulent FIPV challenge on vaccinated cats. In evaluating the immune status of an immunized cat, it is of little value to determine the titer of subunit-specific or neutralizing antibody in sera. To date, there has been no-correlation between specific antibody titers and protection; in fact, cats with high titers of FIPV-specific antibody (neutralizing or not) are generally predisposed or sensitized to enhance disease upon challenge. However, it may be useful to derive a serological profile of immunized cats, particularly when evaluating cross-protection between FIPV Type I and FIPV Type II. The methods for carrying out vaccine trials in cats are as follows.

Cats are vaccinated with two 1 ml doses of candidate vaccines three weeks apart on days 0 and 21. In the case of inactivated vaccines, adjuvants may constitute anywhere from 10–50% of each dose. Inactivated vaccines are delivered intramuscularly. Live vaccines are delivered by scarification, intramuscularly, etc. Vaccinates and controls are challenged on day 35 by the oral/intranasal route with 5 ml of FIPV 79-1146 diluted 1:10,000 and are monitored for fever and ascites fluid. From day 35, the day of challenge, until the end of the study, cats are housed in individual cages with no contact between cats. The cats are bled on days 0, 7, 14, 21, 28, 35, 42, 49, 56, 70, 77, 84, 91, 105, and 112 for IFA on Type I and Type II, SN against Type I and Type II, and anti-FIPV subunit (depending on protein or combination in vaccine) antibody titer. A second challenge is done for survivors five to six weeks after the first challenge.

TABLE 2

Summary of FIPV Vaccine Studies

| VACCINE | | DEATH RATE | | DAY OF DEATH ONSET | | PROTECTION | | TOTAL | AVERAGE |
|---|---|---|---|---|---|---|---|---|---|
| Group | Study | % Deaths/Day | Rank | Day | Rank | % | Rank | Rank | Rank |
| pSC11 N/live | 1 + 2 | 1.207 | 1 | 17.102 | 3 | 41.7 | 1 | 5 | 1.67 |
| Controls | 1 + 2 | 1.218 | 2 | 5.942 | 6 | 25 | 2 | 10 | 3.33 |
| pUV1 N/MG1 | 2 | 1.317 | 3 | 7.333 | 5 | 25 | 2 | 10 | 3.33 |
| pUV1 N/ENM | 1 + 2 | 2.328 | 5 | 15.946 | 4 | 25 | 2 | 11 | 3.67 |
| pUV1 N/AS | 1 | 5.882 | 7 | 21.5 | 1 | 0 | 3 | 11 | 3.67 |
| pUV1 N/live | 1 | 8.48 | 8 | 20 | 2 | 0 | 3 | 13 | 4.33 |
| Whole 1146/AS | 1 | 1.661 | 4 | 4.5 | 7 | 0 | 3 | 14 | 4.67 |
| Whole 1146/ENM | 1 | 2.473 | 6 | −0.286 | 8 | 0 | 3 | 17 | 5.67 |

TABLE 2-continued

Summary of FIPV Vaccine Studies

| VACCINE | | DEATH RATE | | DAY OF DEATH ONSET | | PROTECTION | | TOTAL | AVERAGE |
|---|---|---|---|---|---|---|---|---|---|
| Group | Study | % Deaths/Day | Rank | Day | Rank | % | Rank | Rank | Rank |

The ranking for each category was determined by consecutive relative position. For example, the lowest death rate, the longest period before the onset of death and the greatest degree of protection would receive a rank of 1. The Total Rank is calculated by summing the individual ranks from each category. The Average Rank is calculated by dividing by the total number of categories which is 3.
1) % Deaths per Day—determined from the slope of the line generated by the linear regression analysis of % Deaths vs. Day Post-Challenge plot.
2) Day of Death Onset—determined from the y-axis intercept generated by the linear regression analysis of Day Post-Challenge vs. % Deaths.

The term "FIPV protein" is used in a generic sense to include each of the proteins selected from N, E1, NS1 and NS2. It is possible to use any of the above-mentioned proteins in the diagnostic assays of Examples 7 and 8.

Example 7

Radioimmunoassay Diagnostic Test
7A. Polyclonal Antibody Preparation

The FIPV proteins of Example 5 are purified using standard protein purification techniques. Five mg of a purified FIPV protein is conjugated to keyhole limpet hemocyanin (KLH) with carbodiimide using a two-step procedure. Protein and 5 mg of carbodiimide are incubated in 1 ml of 1 mM HCl for 15 min at 4° C. Nine ml of 1 mM NaOH (25° C.) is added to this mixture followed by 5 mg of KLH. The reaction mixture is shaken overnight at 21° C. and dialyzed against 10 mM $NaH_2PO_4$, 150 mM NaCl (pH 7.4) for 2 days. The FIPV protein/KLH conjugate is emulsified in a 4:6 ratio with complete Freund’s adjuvant and 250 ug protein is injected into 5 kg Male Dutch Belted rabbits subcutaneously in multiple sites or directly into inguinal lymph nodes. The rabbits are boosted with the same preparation I.M. in their hindlegs 3 weeks later. Ten days later the animals are bled and antiserum is collected and analyzed. Using standard enzyme-linked immunoadsorbent assays (E. Engvall, (1972) *J Immunol* 109:129) the ability of the anti-protein and control antisera to bind to various antigens is investigated.

7B. Radioimmunoassdy

The FIPV protein of Example 5 is purified using standard techniques and is iodinated using standard protocols as follows. Iodogen (Pierce Chemical Co. #28666) is dissolved in chloroform to a concentration of 10 ug/ml and 160 ul is added to a glass 12×75 tube and evaporated under a stream of dry nitrogen. Sixty ul of 0.2M sodium phosphate, pH 7.2 is added to the tube. Purified FIPV protein, typically 3 ug, is added to the tube and mixed. The reaction is started by adding a 2-fold molar excess of $Na^{125}I$. Following an incubation for 15 min at room temperature, the reaction is stopped by adding 60 ul of 0.1% sodium metabisulfite and 30 ul of 0.1 mM potassium iodide. The reaction mixture is transferred to a G-50 Sephadex column (0.1 ml bed volume, equilibrated in phosphate-buffered saline), and the flow-through is collected. TCA-precipitable counts are determined and the radioligand is stored at −70° C.

For the radioimmunoasssay, 100 ul samples of FIPV-purified protein standards or white blood celllysates from a cat are aliquoted into replicate glass tubes. To each tube is added 300 ul of iodinated FIPV protein (prepared as above) which has been diluted to contain 150 cpm/ul and 100 ul polyclonal FIPV antibody, from section 7A above, which has been diluted 1/3000. All reagents are diluted in RIA buffer (50 mM sodium phosphate pH 7.4, 5 mM sodium chloride, and 2 mM sodium azide). The reaction mixture is allowed to incubate overnight at room temperature. The next day, 200 ul of goat anti-rabbit IgG which has been diluted 1/10 in RIA buffer is added to the reaction mixture and allowed to incubate overnight at room temperature. The following day, the tubes are centrifuged at 4000 rpm for 30 min, the supernatants are aspirated and the pellets are counted on a gamma counter. A sample which contains many counts has very little FIPV protein in it, while a sample which contains few counts has an appreciable amount of FIPV protein. If desired, a standard curve can be generated and used to determine the amount of FIPV in the sample.

Example 8

ELISA Diagnostic Test

8A. Monoclonal Antibody Preparation

The FIPV proteins of Example 5 are purified using standard protein purification techniques. Eight week-old Balb/c mice are immunized subcutaneously and intraperitoneally with 100 ug of the purified FIPV protein conjugated if necessary and emulsified with adjuvant. The mice are boosted with 50 ug FIPV protein and adjuvant at 2–3 week intervals until a sufficent antiserum titer is achieved. Three days after the final boost, the mice are sacrificed and spleens removed. The spleens are rinsed in a $Ca^{2+}$ and serum-free medium (CSF) described by Schneiderman et al., (1979) *Somatic Cell Genet* 5:263–269, and a single cell suspension is prepared. The suspension is centrifuged at 1000×g for 10 min (Beckman TJ-6), and the pellet is washed three times in 30 ml CSF.

In a parallel manner, 100 ml of SP2/0 myeloma cells, grown to a density of $2\times10^5$ cells/ml are harvested by centrifugation at 1000×g for 10 min. The $2\times10^7$ total cell pellet is washed three times with 30 ml CSF and repelleted. Finally, the spleen cells from above and SP2/0 myeloma cells are combined and pelleted by centrifugation. One ml of polyethylene glycol (PEG MW 1500, Koch-Light Laboratories, Haverhill, England) at a concentration of 37% v/v in CSF is added to the combined pellet over a 90 second period with continual mixing to promote fusion. The PEG is subsequently diluted by the slow addition of 10 ml CSF and cells are repelleted and washed in CSF. The cell pellet is resuspended in HAT selection medium, which contains RPMI 1640, 20% fetal bovine serum, hypoxanthine, aminopterin and thymidine (Littlefield, (1964) *Science* 145:709). The cells are plated into 10×96-well microtiter plates and incubated at 37° C. in 7% $CO_2$. Because the myeloma cells lack the enzyme HPRT, only those SP2/0 cells which have successfully fused with a spleen cell (which provides this enzyme) will survive in the selection medium. The cells are refer with selection medium twice during the next ten days.

After the culture reaches a cell density that covers 75–100% of the microtiter well surface, media from the hybridomas are screened for the presence of anti-FIPV antibody, using an immobilized plate-binding assay (R.H. Kennett et al. eds., *Monoclonal Antibodies* (1980) Plenum Press, New York.). One ug portions of purified FIPV protein diluted in 50 mM sodium bicarbonate, pH 8.3, are incubated in wells of flexible microtiter plates. Following a three-hour incubation at 37° C., wells are washed and 20% gamma globulin-free horse serum is added to occupy nonspecific protein-binding sites. Media from wells containing hybridomas are added and the wells incubated for 2 hours at 37° C. to permit binding of specific antiFIPV antibodies. After the wells are washed again, specifically-bound monoclonal antibodies are detected by incubating $^{125}$I-sheep anti-mouse IgG in the wells for 2 hours at 37° C. Washed wells are cut from the plate and the bound radioactivity is counted. A ratio of three-fold or greater over control binding is considered positive. Hybridomas secreting FIPV-specific antibodies are subcloned and expanded for production and purification of the secreted monoclonal antibody by Protein-A Sepharose.

8B. ELISA Assay

Ninety-six well microtiter plates are coated with 100 ul/well of 10 ug/ml in 50 mM sodium bicarbonate, pH 8.3 of monoclonal antibody prepared in section 8A above. Following an incubation at 37° C. for 90 minutes or at 4° C. for 18 hours, the wells are washed four times with Buffer A (Buffer A is phosphate-buffered saline containing 1% ovalbumin and 0.1% Tween-20. Lysates of feline shite (?) blood cells (diluted 1:10) or purified FIPV protein standards are added to 90–95 ul Buffer A and the wells incubated with this mixture for 90 minutes at room temperature. The wells are again washed four times with Buffer A, and then treated with 100 ul of a 1/5000 dilution in Buffer A of rabbit anti-FIPV as prepared above in Example 7A. After 90 minutes at room temperature, each well is again washed four times with Buffer A. Following this wash, 100 ul of a 1/3000 dilution in Buffer A of goat anti-rabbit IgG peroxidase conjugate (Cappel Laboratories) is added to each well, and the plates are incubated and washed as above. The bound antibody is detected by adding 200 ul of substrate (o-phenylenediamine plus $H_2O_2$ in citric phosphate buffer, pH 5) to each well for 30 min, and color reaction was terminated by the addition of 50 ul 4N sulfuric acid. Absorbance is read at 490 nm in an ELISA reader. FIPV protein concentration in the lysates is determined by comparison with the standard curve.

Modifications of the above described modes for carrying out the invention that are obvious to those of skill in the fields of immunology, recombinant DNA technology and/or veterinary medicine are intended to be within the scope of the following claims.

We claim:

1. A composition for immunizing a cat against feline infectious peritonitis virus (FIPV) infection which composition comprises a non-toxic carrier or diluent and an amount of recombinantly produced E1 protein or N protein of FIPV, or a combination of said E1 protein and said N protein effective to elicit an immune response against FIPV.

2. The composition of claim 1 which further comprises an adjuvant.

3. The composition of claim 1 wherein said recombinantly produced protein is prepared in insect cells from a baculoviral expression vector.

4. The composition of claim 1 which comprises the E1 protein.

5. The composition of claim 4 wherein the E1 protein has the sequence of SEQ ID NO:3.

6. The composition of claim 1 which comprises the N protein.

7. The composition of claim 6 wherein the N protein has the sequence of SEQ ID NO:4.

8. The composition of claim 1 which contains a combination of said E1 protein and said N protein.

9. The composition of claim 8 wherein the E1 protein has the sequence of SEQ ID NO:3 and wherein the N protein has the sequence of SEQ ID NO:4.

10. A method to elicit an immune response in a cat against feline infectious peritonitis virus (FIPV) which method comprises administering to a cat in need thereof a composition which comprises a non-toxic carrier or diluent and an amount of recombinantly produced E1 protein or N protein of FIPV, or a combination of said E1 protein and said N protein effective to elicit said response.

11. The method of claim 10 wherein said composition further comprises an adjuvant.

12. The method of claim 10 wherein said recombinantly produced protein is prepared in insect cells from a baculoviral expression vector.

13. The method of claim 10 wherein said composition comprises the E1 protein.

14. The method of claim 13 wherein the E1 protein has the sequence of SEQ ID NO:3.

15. The method of claim 10 wherein the composition comprises the N protein.

16. The method of claim 15 wherein the N protein has the sequence of SEQ ID NO:4.

17. The composition of claim 10 wherein said composition contains a combination of said E1 protein and said N protein.

18. The method of claim 17 wherein the E1 protein has the sequence of SEQ ID NO:3 and wherein the N protein has the sequence of SEQ ID NO:4.

19. A composition for immunizing a cat against feline infectious peritonitis virus (FIPV) infection which composition comprises a non-toxic carrier or diluent and an amount of virus particles comprising a recombinant expression system comprising a nucleotide sequence encoding the E1 protein or N protein of FIPV operably linked to a control sequence for the expression of said E1 or N protein, effective to elicit an immune response against FIPV.

20. The composition of claim 19 which further comprises an adjuvant.

21. The composition of claim 19 wherein said nucleotide sequence encodes the E1 protein.

22. The composition of claim 21 wherein the E1 protein has the sequence of SEQ ID NO:3.

23. The composition of claim 19 wherein said nucleotide sequence encodes the N protein.

24. The composition of claim 23 wherein the N protein has the sequence of SEQ ID NO:4.

25. The composition of claim 19 wherein said nucleotide sequence encodes both the E1 protein and the N protein.

26. The composition of claim 25 wherein the E1 protein has the sequence of SEQ ID NO:3 and the N protein has the sequence of SEQ ID NO:4.

27. A method to elicit an immune response in a cat against feline infectious peritonitis virus (FIPV) which method comprises administering to a cat in need thereof a composition which comprises a non-toxic carrier or diluent and an amount of virus particles comprising a recombinant expression system comprising a nucleotide sequence encoding the E1 protein or N protein of FIPV operably linked to a control sequence for the expression of said E1 or N protein, effective to elicit said response.

28. The method of claim 25 wherein said composition further comprises an adjuvant.

29. The method of claim 25 wherein said nucleotide sequence encodes the E1 protein.

30. The method of claim 27 wherein the E1 protein has the sequence of SEQ ID NO:3.

31. The method of claim 25 wherein said nucleotide sequence encodes the N protein.

32. The method of claim 29 wherein the N protein has the sequence of SEQ ID NO:4.

33. The method of claim 25 wherein said nucleotide sequence encodes both the E1 protein and the N protein.

34. The method of claim 33 wherein the E1 protein has the sequence of SEQ ID NO:3 and wherein the N protein has the sequence of SEQ ID NO:4.

* * * * *